(12) United States Patent
Christensen et al.

(10) Patent No.: US 8,771,329 B2
(45) Date of Patent: Jul. 8, 2014

(54) METHODS AND APPARATUS FOR ENHANCING VASCULAR ACCESS IN AN APPENDAGE TO ENHANCE THERAPEUTIC AND INTERVENTIONAL PROCEDURES

(75) Inventors: Scott A. Christensen, Danville, CA (US); John Roy Kane, Sierra Vista, AZ (US); Nathan Hamilton, Incline Village, NV (US)

(73) Assignee: CareFusion 2200, Inc., San Diego, CA (US)

( * ) Notice: Subject to any disclaimer, the term of this patent is extended or adjusted under 35 U.S.C. 154(b) by 494 days.

(21) Appl. No.: 12/987,015

(22) Filed: Jan. 7, 2011

(65) Prior Publication Data

US 2011/0172749 A1 Jul. 14, 2011

Related U.S. Application Data

(60) Provisional application No. 61/293,564, filed on Jan. 8, 2010, provisional application No. 61/418,597, filed on Dec. 1, 2010.

(51) Int. Cl.
*A61F 7/00* (2006.01)
*A61F 7/08* (2006.01)

(52) U.S. Cl.
USPC .............................. 607/96; 607/104

(58) Field of Classification Search
USPC ................................. 607/96, 104
See application file for complete search history.

(56) References Cited

U.S. PATENT DOCUMENTS

| | | | |
|---|---|---|---|
| 1,399,095 A | 12/1921 | Webb, Sr. | |
| 3,217,707 A | 11/1965 | Werding | |
| 3,507,321 A | 4/1970 | Palma | |
| 3,859,989 A | 1/1975 | Spielberg | |
| 3,878,839 A | 4/1975 | Norton et al. | |

(Continued)

FOREIGN PATENT DOCUMENTS

| | | |
|---|---|---|
| DE | 19 36 113 | 1/1971 |
| EP | 0 698 387 | 2/1996 |

(Continued)

OTHER PUBLICATIONS

International Search Report, PCT/US2011/020601 dated Sep. 23, 2011.

(Continued)

*Primary Examiner* — Linda Dvorak
*Assistant Examiner* — Kaitlyn Smith
(74) *Attorney, Agent, or Firm* — Brinks Gilson & Lione

(57) ABSTRACT

Embodiments of the invention disclosed herein generally include methods and/or devices for increasing blood flow, controlling the vasodilatation of a patient's vascular structure, regulating the temperature of a portion of a mammal, and for improving various interventional procedures and/or therapeutic techniques. The device may also include one or more access ports, or apertures, that allow access to portions of the mammal's extremity to allow interventional type medical devices, therapeutic devices, surgical support equipment or patient monitoring devices to have access to the extremity on which a body element is disposed. The device may also be configured to allow other supporting components, which may include IV or other catheters, a means of accessing to a portion of the extremity positioned inside the temperature regulating device. In one configuration the device comprises flexible materials that are adapted to conform to the surface of the extremity disposed in the device when a vacuum pressure is applied to an internal region of the device.

20 Claims, 14 Drawing Sheets

(56) References Cited

U.S. PATENT DOCUMENTS

| | | |
|---|---|---|
| 3,894,213 A | 7/1975 | Agarwala |
| 4,149,541 A | 4/1979 | Gammons et al. |
| 4,186,294 A | 1/1980 | Bender |
| 4,204,547 A | 5/1980 | Allocca |
| 4,338,944 A | 7/1982 | Arkans |
| 4,523,594 A | 6/1985 | Kuznetz |
| 4,530,350 A | 7/1985 | Brown et al. |
| 4,624,244 A | 11/1986 | Taheri |
| 4,648,392 A | 3/1987 | Cartier et al. |
| 4,658,823 A | 4/1987 | Beddoe et al. |
| 4,844,072 A | 7/1989 | French et al. |
| 5,035,003 A | 7/1991 | Rinehart |
| 5,050,613 A | 9/1991 | Newman et al. |
| 5,074,285 A | 12/1991 | Wright |
| 5,149,331 A | 9/1992 | Ferdman et al. |
| 5,183,039 A | 2/1993 | Sarian et al. |
| 5,230,333 A | 7/1993 | Yates et al. |
| 5,241,951 A | 9/1993 | Mason et al. |
| 5,241,958 A | 9/1993 | Noeldner |
| 5,314,455 A | 5/1994 | Johnson, Jr. et al. |
| 5,330,519 A | 7/1994 | Mason et al. |
| 5,344,436 A | 9/1994 | Fontenot et al. |
| 5,369,807 A | 12/1994 | Cho et al. |
| 5,417,720 A | 5/1995 | Mason |
| 5,437,610 A | 8/1995 | Cariapa et al. |
| 5,441,477 A | 8/1995 | Hargest |
| 5,443,488 A * | 8/1995 | Namenye et al. ............. 607/104 |
| 5,476,490 A | 12/1995 | Silver |
| 5,507,792 A | 4/1996 | Mason et al. |
| 5,575,762 A | 11/1996 | Peeler et al. |
| 5,620,621 A | 4/1997 | Sontag |
| 5,634,889 A | 6/1997 | Gardner et al. |
| 5,649,954 A | 7/1997 | McEwen |
| 5,662,695 A | 9/1997 | Mason et al. |
| 5,683,428 A | 11/1997 | Franberg et al. |
| 5,683,438 A | 11/1997 | Grahn |
| 5,688,225 A | 11/1997 | Walker |
| 5,729,653 A | 3/1998 | Magliochetti et al. |
| 5,746,213 A | 5/1998 | Marks |
| 5,755,756 A | 5/1998 | Freedman, Jr. et al. |
| 5,817,147 A * | 10/1998 | Wolf ............................. 607/104 |
| 5,865,841 A | 2/1999 | Kolen et al. |
| 5,868,690 A | 2/1999 | Eischen, Sr. |
| 5,913,886 A | 6/1999 | Soloman |
| 5,941,907 A * | 8/1999 | Augustine .................... 607/104 |
| 5,951,949 A | 9/1999 | Olsen |
| 5,960,475 A | 10/1999 | Fewtrell |
| 5,980,561 A | 11/1999 | Kolen et al. |
| 5,997,816 A | 12/1999 | McIntosh et al. |
| 6,144,444 A | 11/2000 | Haworth et al. |
| 6,149,674 A | 11/2000 | Borders |
| 6,197,045 B1 | 3/2001 | Carson |
| 6,203,567 B1 * | 3/2001 | Augustine .................... 607/104 |
| 6,226,552 B1 | 5/2001 | Staunton et al. |
| 6,238,427 B1 | 5/2001 | Matta |
| 6,245,094 B1 | 6/2001 | Pompei |
| 6,268,595 B1 | 7/2001 | Haenel |
| 6,277,143 B1 | 8/2001 | Klatz et al. |
| 6,286,144 B1 | 9/2001 | Henderson et al. |
| 6,296,617 B1 | 10/2001 | Peeler et al. |
| 6,319,214 B1 | 11/2001 | Wortman et al. |
| 6,375,674 B1 | 4/2002 | Carson |
| 6,440,093 B1 | 8/2002 | Nakane et al. |
| 6,446,512 B2 | 9/2002 | Zimmerman et al. |
| 6,461,379 B1 | 10/2002 | Carson et al. |
| 6,488,643 B1 | 12/2002 | Tumey et al. |
| 6,517,510 B1 | 2/2003 | Stewart et al. |
| 6,557,704 B1 | 5/2003 | Randolph |
| 6,565,593 B2 | 5/2003 | Diana |
| 6,576,003 B2 | 6/2003 | Kotack |
| 6,581,400 B2 | 6/2003 | Augustine et al. |
| 6,602,277 B2 | 8/2003 | Grahn et al. |
| 6,620,187 B2 | 9/2003 | Carson et al. |
| 6,645,232 B2 | 11/2003 | Carson |
| 6,648,905 B2 | 11/2003 | Hoglund et al. |
| 6,656,208 B2 | 12/2003 | Grahn et al. |
| 6,660,027 B2 | 12/2003 | Gruszecki et al. |
| 6,666,879 B2 | 12/2003 | Arnold et al. |
| 6,669,715 B2 | 12/2003 | Hoglund et al. |
| D485,338 S | 1/2004 | Augustine et al. |
| 6,673,099 B2 | 1/2004 | Grahn et al. |
| 6,679,432 B1 | 1/2004 | Arnold |
| 6,692,518 B2 | 2/2004 | Carson |
| 6,695,872 B2 | 2/2004 | Elkins |
| 6,699,267 B2 | 3/2004 | Voorhees et al. |
| 6,718,785 B2 | 4/2004 | Bieberich |
| 6,763,728 B1 | 7/2004 | Albrecht |
| 6,764,502 B2 | 7/2004 | Bieberich |
| 6,775,473 B2 | 8/2004 | Augustine et al. |
| 6,786,879 B1 | 9/2004 | Bolam et al. |
| 6,802,855 B2 | 10/2004 | Ellingboe et al. |
| 6,827,728 B2 | 12/2004 | Ellingboe et al. |
| 6,830,049 B2 | 12/2004 | Augustine et al. |
| 6,840,915 B2 | 1/2005 | Augustine |
| 6,855,158 B2 | 2/2005 | Stolpmann |
| 6,876,884 B2 | 4/2005 | Hansen et al. |
| 6,921,374 B2 | 7/2005 | Augustine |
| 6,966,922 B2 | 11/2005 | Grahn et al. |
| 6,974,428 B2 | 12/2005 | Knutson et al. |
| 6,974,442 B2 | 12/2005 | Grahn et al. |
| 6,987,209 B2 | 1/2006 | Augustine et al. |
| 6,988,423 B2 | 1/2006 | Bolam et al. |
| 7,001,416 B2 | 2/2006 | Augustine et al. |
| 7,010,221 B2 | 3/2006 | Augustine et al. |
| 7,014,431 B2 | 3/2006 | Hansen et al. |
| 7,041,123 B2 | 5/2006 | Stapf et al. |
| 7,074,982 B2 | 7/2006 | Knutson et al. |
| 7,087,807 B2 | 8/2006 | Stapf |
| 7,090,692 B1 | 8/2006 | Augustine et al. |
| 7,100,394 B2 | 9/2006 | Bieberich et al. |
| 7,101,389 B1 | 9/2006 | Augustine et al. |
| 7,108,713 B1 | 9/2006 | Augustine |
| 7,120,951 B2 | 10/2006 | Augustine et al. |
| 7,122,046 B2 | 10/2006 | Augustine et al. |
| 7,122,047 B2 | 10/2006 | Grahn et al. |
| 7,164,852 B2 | 1/2007 | Cazzini et al. |
| 7,182,776 B2 | 2/2007 | Grahn et al. |
| 7,220,273 B2 | 5/2007 | Van Duren et al. |
| 7,226,454 B2 | 6/2007 | Albrecht et al. |
| 7,232,457 B2 | 6/2007 | Schmidt et al. |
| 7,244,268 B2 | 7/2007 | Arnold et al. |
| 7,264,630 B1 | 9/2007 | Webb |
| 7,303,579 B2 * | 12/2007 | Schock et al. ................ 607/104 |
| 7,351,254 B2 | 4/2008 | Magers |
| 7,361,186 B2 | 4/2008 | Voorhees et al. |
| 7,422,576 B2 | 9/2008 | Boynton et al. |
| 7,666,213 B2 * | 2/2010 | Freedman et al. ............ 607/104 |
| 7,871,428 B2 * | 1/2011 | Augustine .................... 607/107 |
| 8,105,370 B2 * | 1/2012 | Augustine .................... 607/107 |
| 2002/0007201 A1 | 1/2002 | Grahn et al. |
| 2002/0019653 A1 | 2/2002 | Grahn et al. |
| 2002/0022791 A1 | 2/2002 | Morris et al. |
| 2002/0142894 A1 | 10/2002 | Flynn |
| 2003/0024684 A1 | 2/2003 | Lyons et al. |
| 2003/0040783 A1 | 2/2003 | Salmon |
| 2003/0097163 A1 | 5/2003 | Kane et al. |
| 2003/0125649 A1 | 7/2003 | McIntosh et al. |
| 2003/0191437 A1 | 10/2003 | Knighton et al. |
| 2004/0024322 A1 | 2/2004 | Caspers |
| 2004/0073146 A1 | 4/2004 | Weintraub et al. |
| 2004/0077978 A1 | 4/2004 | Nelson et al. |
| 2004/0106884 A1 | 6/2004 | Bolam et al. |
| 2004/0162571 A1 | 8/2004 | Rabiner et al. |
| 2004/0223962 A1 | 11/2004 | Riordan |
| 2004/0225341 A1 * | 11/2004 | Schock et al. ................ 607/104 |
| 2005/0027218 A1 | 2/2005 | Filtvedt et al. |
| 2005/0033392 A1 | 2/2005 | Belzidsky |
| 2005/0065583 A1 | 3/2005 | Voorhess et al. |
| 2005/0070954 A1 | 3/2005 | Johnson et al. |
| 2005/0096714 A1 * | 5/2005 | Freedman et al. ............ 607/104 |
| 2005/0131489 A1 | 6/2005 | Gardon-Mollard |
| 2005/0159690 A1 | 7/2005 | Barak et al. |
| 2005/0209663 A1 | 9/2005 | Hamilton et al. |
| 2005/0209665 A1 | 9/2005 | Hunter et al. |

(56) References Cited

U.S. PATENT DOCUMENTS

| | | |
|---|---|---|
| 2005/0222526 A1 | 10/2005 | Perry et al. |
| 2005/0251067 A1 | 11/2005 | Terry |
| 2005/0256556 A1 | 11/2005 | Schirrmacher et al. |
| 2006/0016012 A1 | 1/2006 | Liu |
| 2006/0058858 A1 | 3/2006 | Smith |
| 2006/0074362 A1 | 4/2006 | Roso et al. |
| 2006/0111766 A1 | 5/2006 | Grahn et al. |
| 2006/0122670 A1 | 6/2006 | Grahn et al. |
| 2006/0150792 A1 | 7/2006 | Cazzini et al. |
| 2007/0060987 A1 | 3/2007 | Grahn et al. |
| 2007/0123962 A1 | 5/2007 | Grahn et al. |
| 2007/0142887 A1 | 6/2007 | Cazzini et al. |
| 2008/0021531 A1 | 1/2008 | Kane et al. |
| 2008/0064992 A1 | 3/2008 | Stewart et al. |
| 2008/0077205 A1 | 3/2008 | Cazzini |
| 2008/0132816 A1* | 6/2008 | Kane et al. .................. 601/152 |
| 2008/0132976 A1* | 6/2008 | Kane et al. .................. 607/104 |
| 2008/0177232 A1 | 7/2008 | Knighton et al. |
| 2008/0208088 A1 | 8/2008 | Cazzini et al. |
| 2008/0249593 A1 | 10/2008 | Cazzini et al. |
| 2009/0036959 A1 | 2/2009 | Filtvedt et al. |
| 2009/0048649 A1 | 2/2009 | Peret et al. |
| 2009/0099629 A1 | 4/2009 | Carson et al. |
| 2009/0112298 A1 | 4/2009 | Jusiak et al. |
| 2009/0177184 A1 | 7/2009 | Christensen et al. |
| 2009/0312675 A1 | 12/2009 | Sampson et al. |
| 2010/0210982 A1 | 8/2010 | Balachandran et al. |
| 2011/0021960 A1 | 1/2011 | Filtvedt et al. |
| 2011/0238143 A1 | 9/2011 | Schock et al. |
| 2011/0264063 A1 | 10/2011 | Weston |
| 2011/0301510 A1 | 12/2011 | Filtvedt et al. |

FOREIGN PATENT DOCUMENTS

| | | |
|---|---|---|
| EP | 1 929 980 | 4/2007 |
| FR | 2544202 | 10/1984 |
| WO | WO 96/28120 | 9/1996 |
| WO | WO 96 28888 | 9/1996 |
| WO | WO 98/40039 | 9/1998 |
| WO | WO 01/80790 | 11/2001 |
| WO | WO 02/085266 | 10/2002 |
| WO | WO 03/045289 | 6/2003 |

OTHER PUBLICATIONS

European Office Action, Application No. 07015200.4 dated Oct. 5, 2011 (with EP Search Report).

Morris et al., "Evidence-Based Compression: Prevention of Stasis and Deep Vein Thrombosis", Annals of Surgery 239(2), pp. 162-171, Feb. 2004, (C) 2004 Lippincott Williams & Wilkins, Inc.

Frank et al., "Relative Contribution of Core and Cutaneous Temperatures to Thermal Comfort and Autonomic Responses in Humans", Journal of Applied Physiology, vol. 86, Issue 5, pp. 1588-1593, May 1999, http://jap.physiology.org/cgi/content/full/86/5/1588#BIBL.

Herrman et al., "Skin Perfusion Responses to Surface Pressure-Induced Ischemia: Implication for the Developing Pressure Ulcer", Journal of Rehabilitation Research & Development, vol. 36 No. 2, Apr. 1999, 20 pages.

De Witte et al, "Perioperative Shivering, Physiology and Pharmacology", Anesthesiology, vol. 96 No. 2, Feb. 2002, pp. 467-484, http://www.or.org/Reviews/four/review.html.

Grahn et al., "Recovery from Mild Hypothermia Can Be Accelerated by Mechanically Distending Blood Vessels in the Hand", J Applied Physiol 85(5): pp. 1643-1648, 1998.

Walsh et al., "Blood Flow, Sympathetic Activity and Pain Relief following Lumbar Sympathetic Blockade or Surgical Sympathectomy", Anesthesia Intensive Care 13(1), pp. 18-24 , Feb. 1985.

Kulkarni et al., "Negative Pressure Applied to the Foot Decreases the Body-Core: Great-Toe Temperature Gradient", Abstract, Department of Anesthesia, Stanford University, Stanford, CA, Oct. 13, 2007. http://www.asaabstracts.com/strands/asaabstracts/abstract.htm;jsessionid=370D6FEE1329050C935DFC3A4EBFB325?year=2007&index=8&absnum=1052.

Sessler, Daniel I., "Complications and Treatment of Mild Hypothermia", Anesthesiology 95(2), pp. 531-543, Aug. 2001.

Esburg et al: "Mechanical Characteristics of Human Skin Subject to Static vs Cyclic Normal Pressures". JRRD, vol. 36, No. 2, 1999, http://www.rehab.research.va.gov/jour/99/36/2/edsberg.pdf.

Eldar Soreide, et al., "A Non-Invasive Means to Effectively Restore Normothermia in Cold Stressed Individuals: A Preliminary Report," The Journal of Emergence Medicine, 1999, pp. 725-730, vol. 17, No. 4, U.S.A.

Dennis Grahn, "Hypothermia in Trauma-Deliberate or Accidental," Trauma Care '97, 10th Annual Trauma Anesthesia and Critical Care Symposium and World Exposition, May 15-17, 1997, pp. i and 1-21, Baltimore.

Michael McEwan, "Hypothermia—Physiology, Signs, Symptoms and Treatment Considerations," Search and Rescue Society of British Columbia, www.sarbc.org/hypo1.html, Oct. 28, 1995, pp. 1-6.

Office Action, U.S. Appl. No. 11/566,575 dtd Feb. 18, 2011.

Office Action, U.S. Appl. No. 11/830,486 dtd Mar. 1, 2011.

Office Action, U.S. Appl. No. 11/945,999 dtd Apr. 13, 2011.

Radial Artery Access, "For Angioplasty and Stent Procedures". Texas Heart Institute. Oct. 2010.

Layton, et al. "The Radial Artery Access Site for Interventional Neuroradiology Procedures", www.ajnr.org. AJNR Am J. Neuroradiol 27:1151-51. May 2006.

DeviceTalk. Medical Device and Diagnostic Industry. "Wrist and Reward for Stents", Oct. 2010.

European Search Report. EP 08 15 3151 dated Apr. 7, 2011.

* cited by examiner

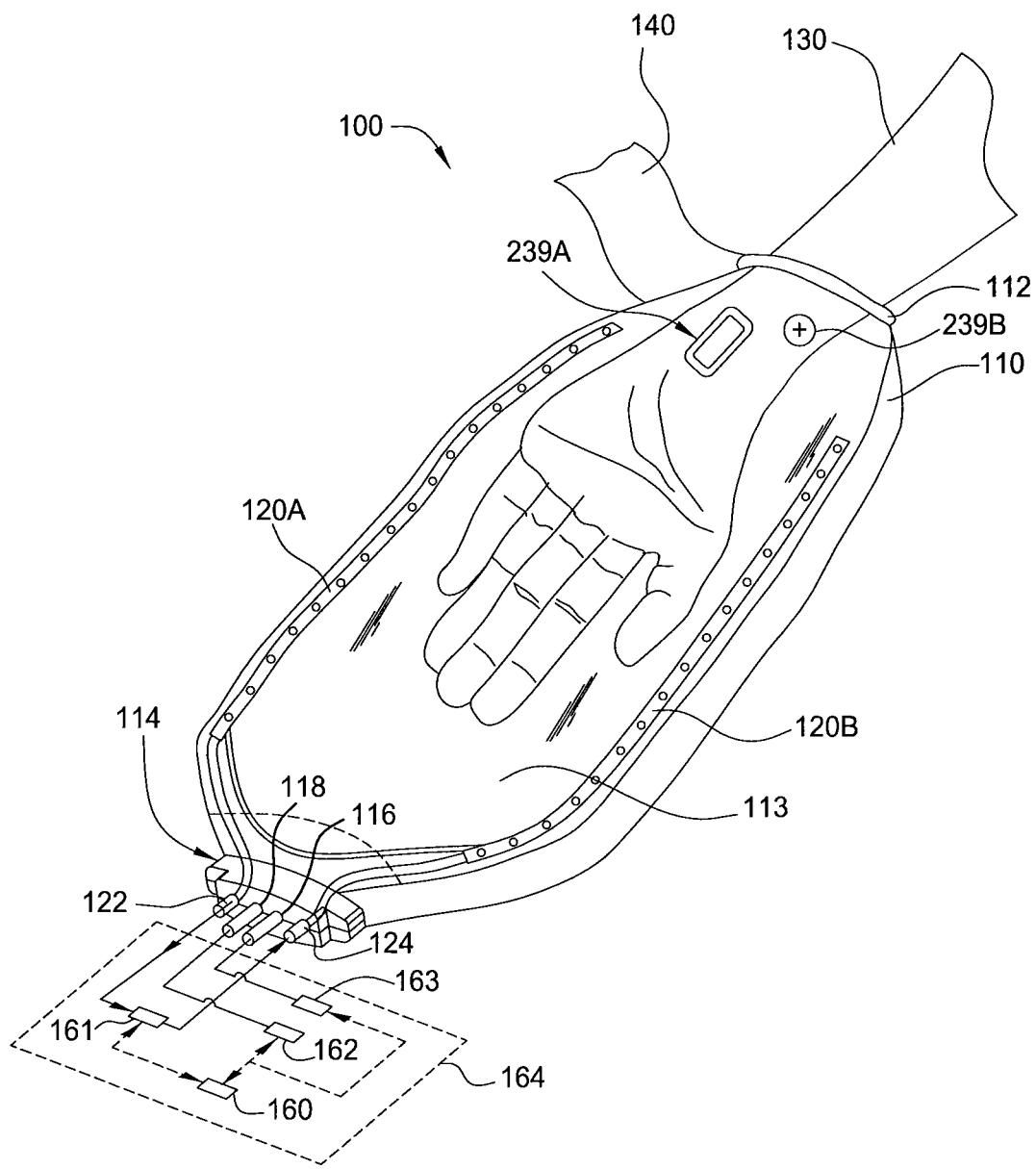

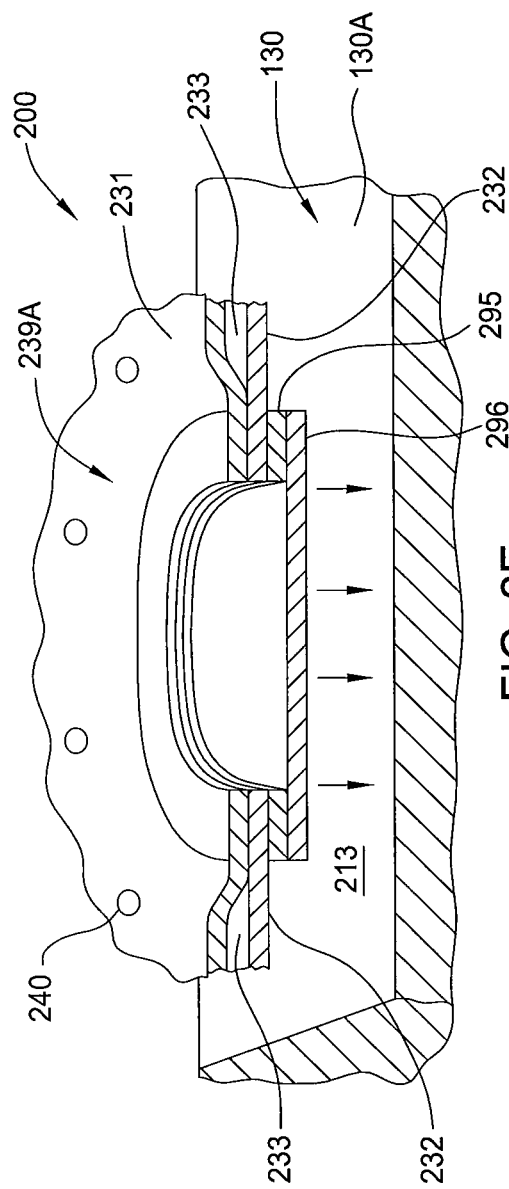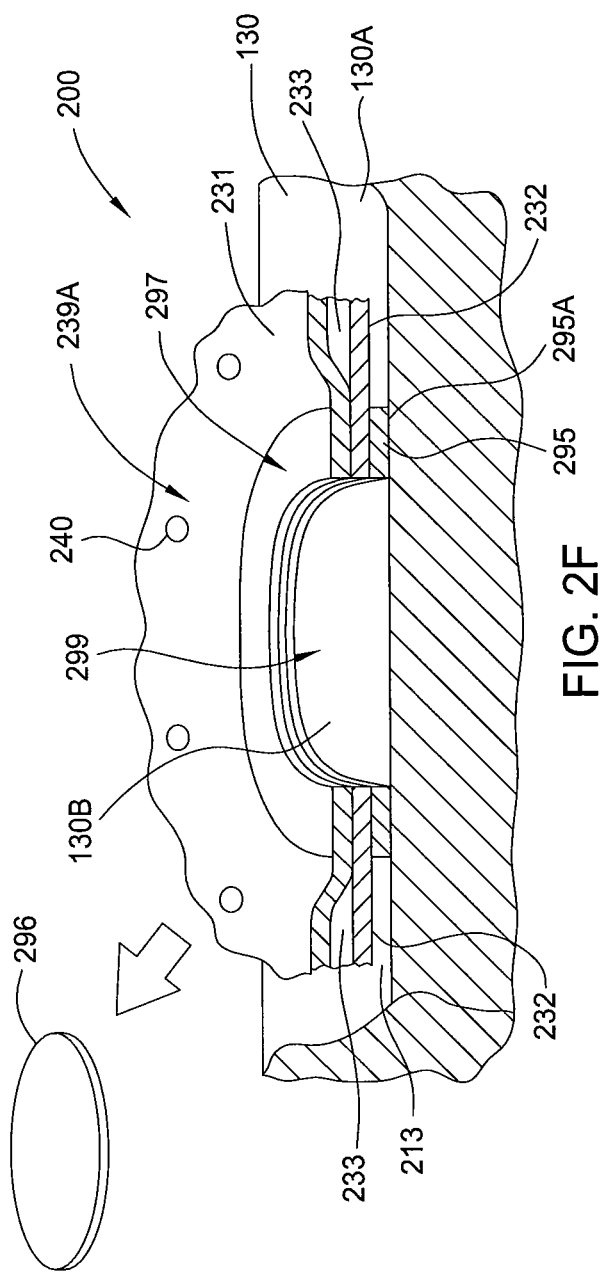

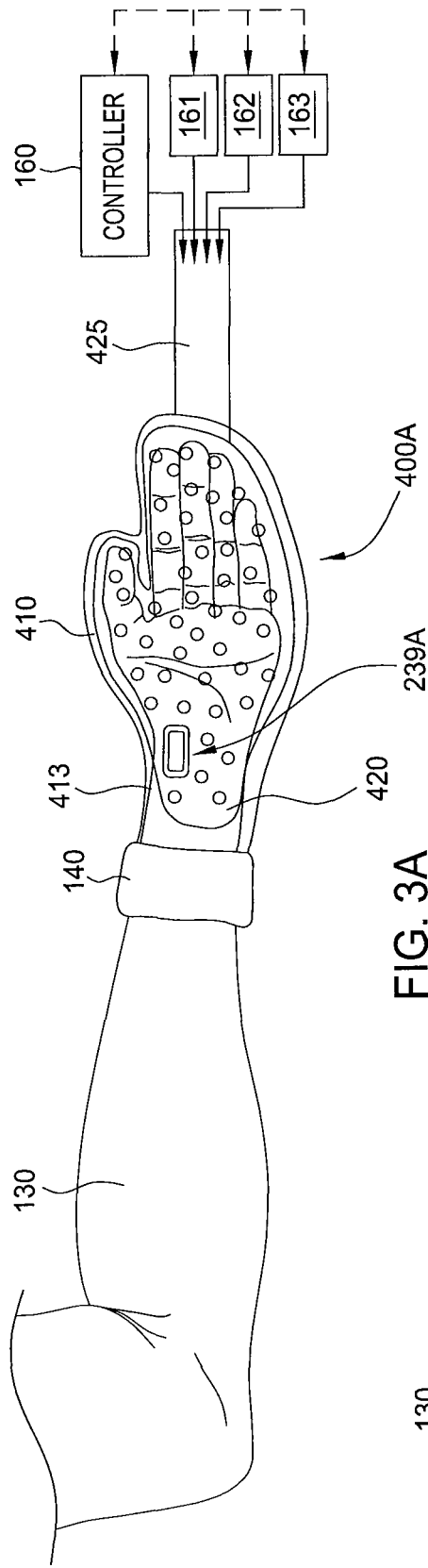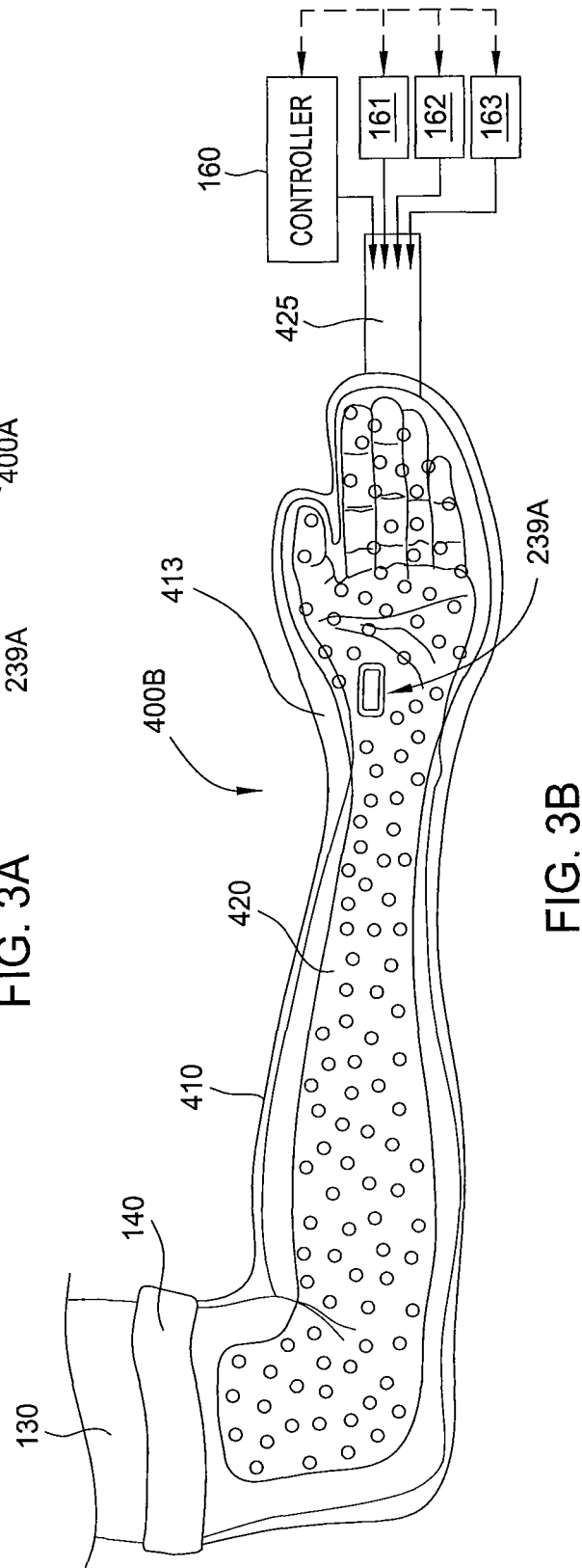
FIG. 3A
FIG. 3B

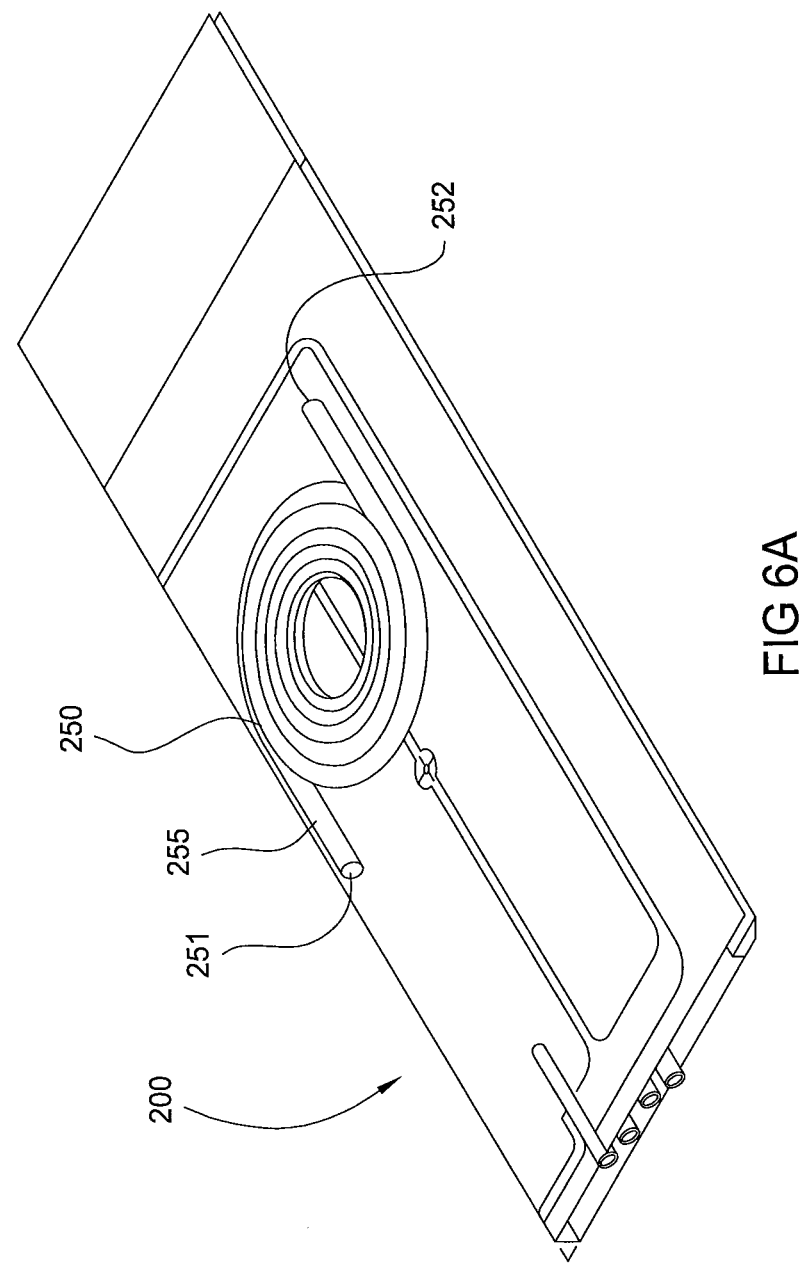

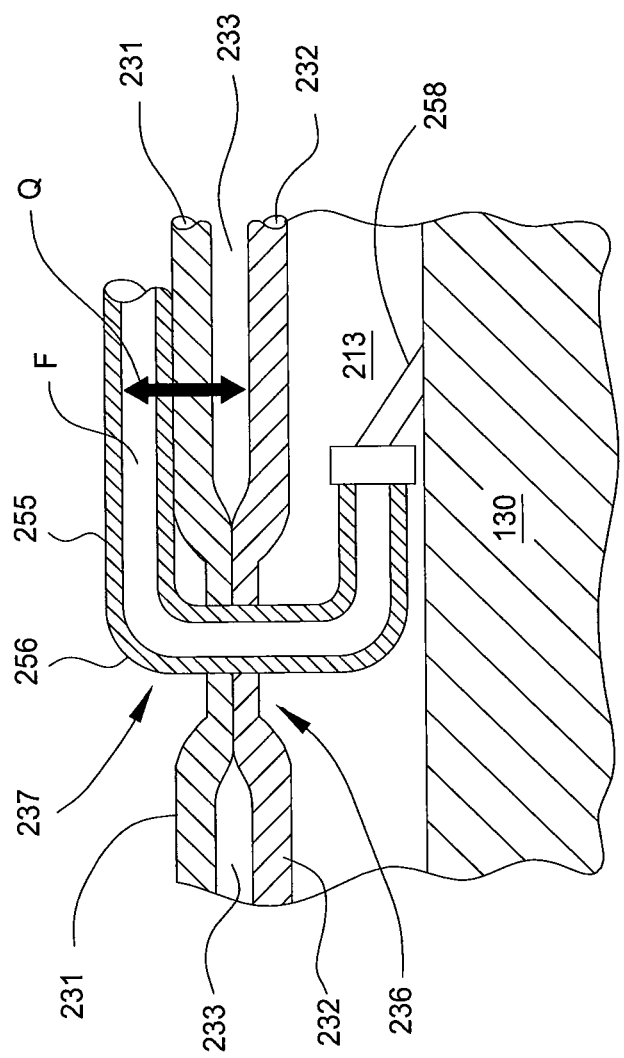
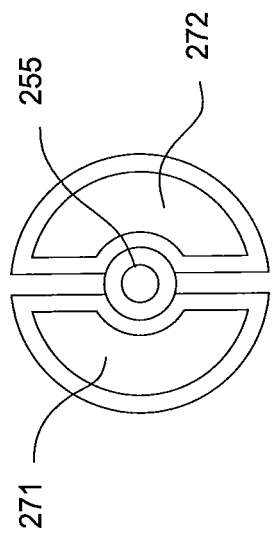
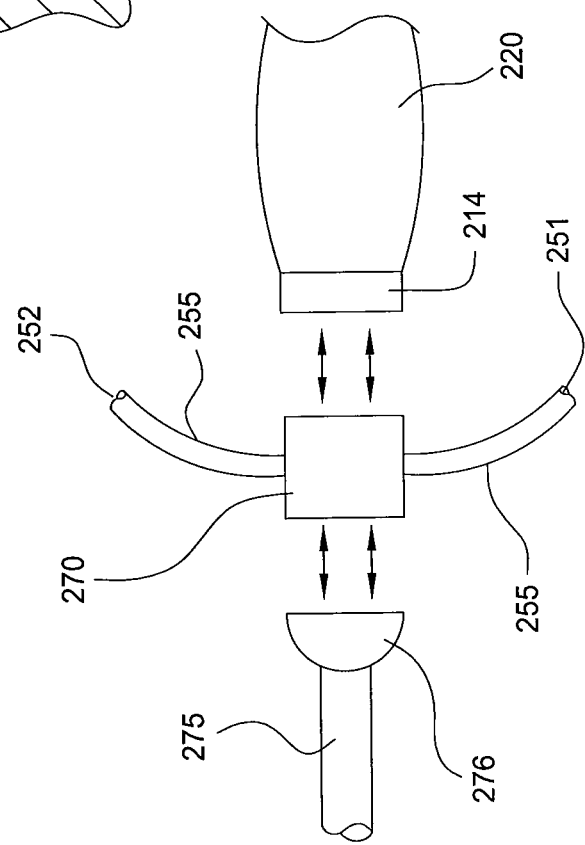
FIG 6C
FIG 6E
FIG 6D

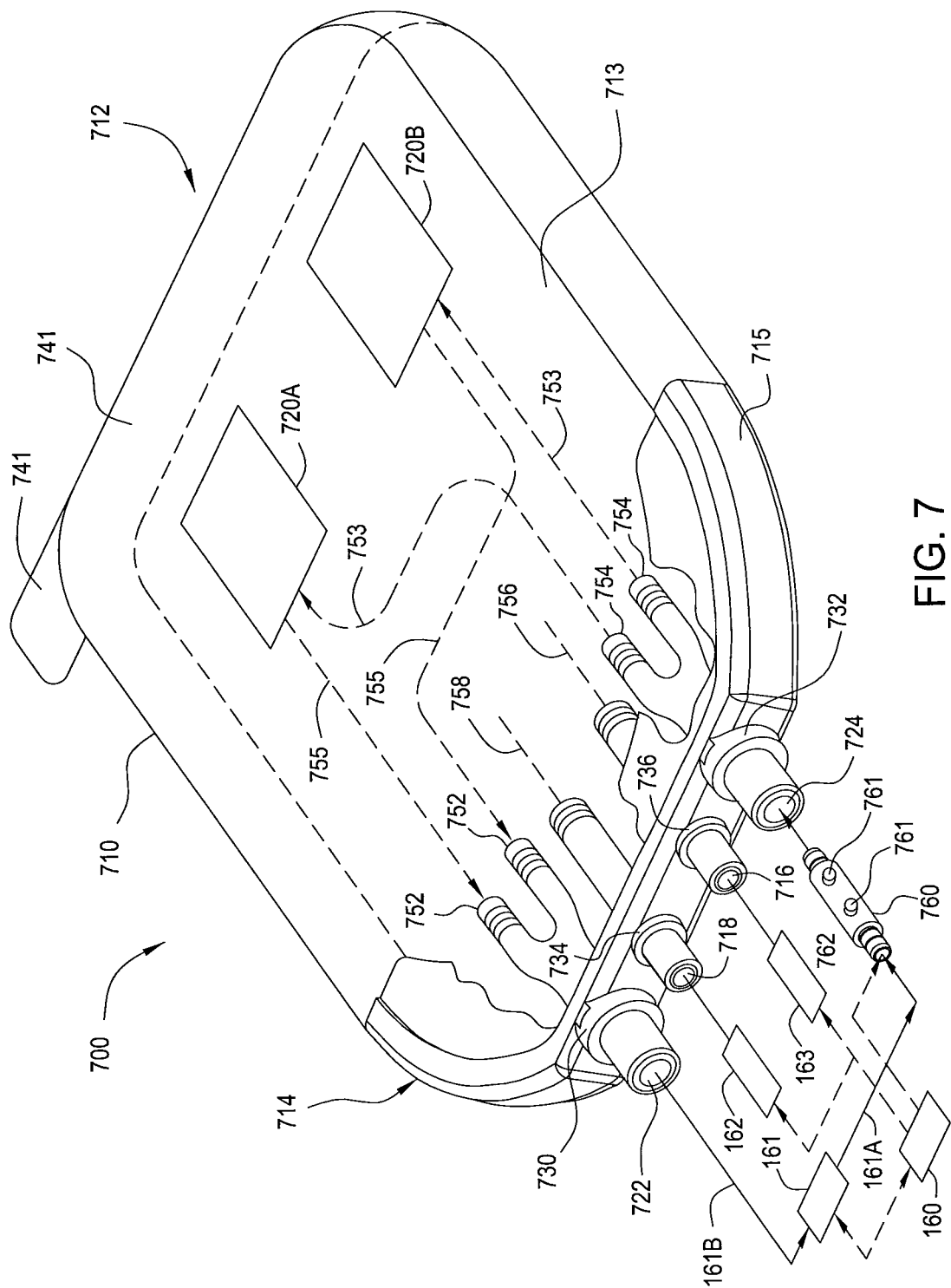

METHODS AND APPARATUS FOR ENHANCING VASCULAR ACCESS IN AN APPENDAGE TO ENHANCE THERAPEUTIC AND INTERVENTIONAL PROCEDURES

CROSS-REFERENCE TO RELATED APPLICATIONS

This application claims benefit of U.S. Provisional Patent Application Ser. No. 61/293,564, filed Jan. 8, 2010, and U.S. Provisional Patent Application Ser. No. 61/418,597, filed Dec. 1, 2010, which are both incorporated by reference herein.

BACKGROUND OF THE INVENTION

1. Field of the Invention

Embodiments of the invention generally relate to methods and apparatus for increasing blood flow and/or adjusting and maintaining the core temperature of a human.

2. Description of the Related Art

Homoiothermic animals, such as humans, strive to maintain relatively constant internal temperatures despite temperature variations in ambient environments and fluctuations in internal heat released as a byproduct of cellular metabolism. In humans, the thermal core generally includes the vital organs of the body, such as the brain and the several organs maintained within the abdomen and chest. Peripheral tissues, such as the skin, fat, and muscles, act as a buffer between the thermal core and the external environment of the animal by maintaining a temperature gradient that ranges from near-core temperature within internal organs to near-ambient temperature at the surface of the animal or other mammals.

Mammalian temperature regulation requires adaptations mechanisms, such as insulation, respiratory heat conservation, and passive heat dissipation, etc., to enable mammalian survival without excessive resource expenditure to generate a stable internal thermal environment. Insulation, internal or external, impedes heat transfer from ambient condition to the body core and also protects animals from the cold. Subcutaneous insulation, similarly, retards the transfer of heat from the skin surface into the body core. The insulative properties of peripheral tissues are determined by blood flow through the tissues and in the absence of blood flow, heat transfer through the tissues is negligible. For example, lack of blood flow and poor blood perfusion makes adipose tissues good insulators. Any tissues that are poorly perfused may become insulators. Tissue blood perfusion determines local heat transfer and enables delivery of heat to (or removal from) a body region.

Respiratory heat conservation is an adaptive mechanism to prevent heat loss, heat exchange between the circulating blood and the air at the gas exchange surface of the lung alveoli in mammals. All of the circulating blood passes through the gas exchange surfaces of the lungs.

Heat is dissipated to the environment from the thermal core to the body surface by delivering through blood flow within the confines of the circulatory system. The distribution of the systemic blood is in accordance with local tissue metabolic demand. All blood passes through the chambers of the heart and the lungs. Cardiac output in a resting human is about 5 L/min so that the total blood volume circulates at a turnover rate of one cycle per minute. Blood volume and cardiac output in mammals are insufficient to uniformly perfuse all tissues in the body. Specialized vascular structures promote heat exchange in the blood flow.

Two types of vascular structures are found in mammals: nutrient vascular units and heat exchange vascular units. Their functions are mutually exclusive: The nutrient vascular units contain thin-walled, small diameter blood vessels uniformly distributed throughout the skin, such as arterioles, capillaries, and venules, and require slow blood flow through to provide nutrients to local tissues. The heat exchange vascular units contain thick-walled, large diameter venules, such as venous plexuses and Arteriovenous Anastomoses (AVAs; vascular communications between small arteries and the venous plexuses), and require flowing of large blood volumes to promote heat dissipation. In humans, the venous plexuses and AVAs of the heat exchange vascular units in humans are found mainly in the non-insulated palms of the hands, soles of the feet, ears, and non hairy regions of the face.

The thermoregulatory system in homoiothermic animals can be compromised (e.g., by anesthesia, trauma, or other factors) and may lead to the various thermal maladies and diseases. Under general anesthesia, a patient may be induced to loss the ability to conserve bodily heat. Thermal maladies, such as hypothermia and hyperthermia, can occur when the thermoregulatory system is overwhelmed by severe environmental conditions. Constriction of the AVAs thermally isolates the body core from the environment, while, dilation of the AVAs promotes a free exchange of heat between the body core and the environment.

Blood flow through the heat exchange vascular structures can be extremely variable, for example, high volume of blood flow during heat stress or hyperthermia can be increase to as high as 60% of the total cardiac output. Hypothermia, on the other hand, is the result of prolonged exposure to a cold challenge where blood flow through the venous plexuses and AVAs can be near zero of the total cardiac output. Vasoconstriction of the peripheral blood vessels may arise under hypothermia in order to prevent further heat loss by limiting blood flow to the extremities and reducing heat transfer away from the thermal core of the body. However, vasoconstriction makes it much more difficult to reverse a hypothermic state since vasoconstriction impedes the transfer of heat from the body surface to the thermal core and makes it difficult to simply apply heat to the surface of the body. This physiological impediment to heat transfer is referred to as a vasoconstrictive blockade to heat exchange. There is a need to regulate blood flow to the venous plexuses and AVAs of the heat exchange vascular units and intervene thermal maladies.

Other thermal malady related diseases, such as venous thromboembolic disease, continues to cause significant morbidity and mortality. Hospitalization due to venous thrombosis and pulmonary embolism (PE) ranges from 300,000 to 600,000 persons a year. Following various types of surgical procedures, as well as trauma and neurological disorders, patients are prone to developing deep vein thrombosis (DVT) and PE, which usually originate from blood clots in the veins and some clots traveling to the lung. Regardless of the original reasons for hospitalization, one in a hundred patients upon admission to hospitals nationwide dies of PE. Patients suffering from hip, tibia and knee fractures undergoing orthopedic surgery, spinal cord injury, or stroke are especially at high risk. Thus, prevention of DVT and PE is clinically important.

It is believed that slowing of the blood flow or blood return system from the legs may be a primary factor related to DVT with greatest effect during the intraoperative phase. Also of concern is the postoperative period. Even individuals immobilized during prolong travel on an airplane or automobile may be at risk. Generally, without mobility, return of the blood back to heart is slowed and the veins of an individual rely only on vasomotor tone and/or limited contraction of soft muscles to pump blood back to the heart. One study shows that travel trips as short as three to four hours can induce DVT and PE.

Current approaches to prophylaxis include anticoagulation therapy and mechanical compression to apply pressure on the muscles through pneumatic compression devices. Anticoagulation therapy requires blood thinning drugs to clear clots in the veins which must be taken several days in advance to be effective. In addition, these drugs carry the risk of bleeding complications. Pneumatic compression devices, which mechanically compress and directly apply positive message-type pressures to muscles in the calf and foot sequentially, are not comfortable, are difficult to use even in a hospital, and are too cumbersome for mobile patients or for use during prolonged travel. In addition, most of them are heavy weighted and there are no portable or user friendly devices.

U.S. Pat. No. 5,683,438, issued to Grahn and assigned to Stanford University, discloses an apparatus and method for overcoming the vasoconstrictive blockade to heat exchange by mechanically distending blood vessels in a body portion and providing heat transfer to the body core of a hypothermic mammal. The disclosed device comprises a fluid-filled heating blanket that is lodged within a tubular, elongated hard shelled sleeve placed over the body portion. Sub-atmospheric pressure is applied and maintained within the sleeve. However, most devices for regulating body temperature may not provide sufficient heat or adequate surface area for heat transfer being optimized and evenly distributed between the heating element and the body of the patient. In addition, the devices may not be able to adapt to the variability in patient sizes or provide mobility of the body portion during prolong treatment. Further, the devices may also allow access to the extremity during treatment or be able to regulate the temperature of fluids injected intravenously (IV) into the body.

Therefore, there remains a need for an apparatus and method to increase blood flow to the venous plexuses and AVAs of the heat exchange vascular units, thereby reducing the vasoconstrictive blockade and promoting heat exchange for body temperature regulation and disease intervention.

SUMMARY OF THE INVENTION

Embodiments of the invention provide methods and an apparatus for exchanging heat with an extremity of a mammal and/or enhancing various interventional, therapeutic or surgical procedures. In one embodiment, a device is provided for regulating temperature and/or providing a vacuum or a negative pressure on an extremity of a mammal, such as a hand, an arm, a leg, foot, or calf of a leg, in order to increase blood flow on the extremity. The device may also be configured to allow other supporting components, which may include IV tubing or catheter, a means of accessing to a portion of the extremity positioned inside the temperature regulating device. In one case, the device is used to control the size of the vascular structures in a patient to allow various arteries or veins to more easily accept a catheter during interventional or therapeutic procedures. The device may also be configured to regulate the temperature of fluids injected intravenously into the body. In one embodiment, an IV tubing set is placed in proximity to a heat exchange fluid in a thermal exchanging unit in the device. In one configuration the device comprises flexible materials that are adapted to conform to the surface of the extremity disposed in the device when a vacuum pressure is applied to an internal region of the device. According to an embodiment of the invention, a flexible extremity device can be used in combination with a mechanical compression device or the flexible extremity device can itself be modified to include one or more pressure-applying gas plenums in order to apply pressurized compression forces to a extremity of a mammal, in addition to regulating the temperature and/or applying vacuum to the space between the extremity and device.

Some embodiments of the invention provide an apparatus for exchanging heat with an extremity of a mammal and/or controlling body temperature, comprising a body element having one or more walls that enclose an internal region, an opening formed in the body element that is adapted to receive an extremity of a mammal and allow a portion of the extremity to be positioned within the internal region, one or more thermal exchanging units that are disposed in thermal contact with the internal region, and an aperture in the body element, wherein the aperture provides access to the portion of the extremity positioned within the internal region. The aperture may be adapted to receive an IV tube, a catheter and/or sensing devices. The device may also comprise a flow path for IV fluids in proximity to at least one of the thermal exchanging units, such that heat may transfer between the flow path for IV fluids and the thermal exchanging unit. The flow path for IV fluids may comprise an IV tubing set. The IV tubing set may also be heat welded to the thermal exchanging unit. Alternatively, an adhesive sheet may be positioned over the IV tubing set and the thermal exchanging unit.

Embodiments may provide an apparatus for exchanging heat with an extremity of a mammal and/or controlling body temperature further comprising an extremity sealing member that is adapted to form a seal between the body element and a portion of the extremity, and a port sealing member that is adapted to form a seal over the port and any device inserted therein. The device may also comprise a pump that is adapted to control the pressure within the internal region to improve the thermal contact between the one or more thermal exchange units and the surface of the portion of the extremity. The internal region may be maintained at a pressure between about −3 mmHg and about −80 mmHg relative to the pressure outside the one or more walls of the body element.

Embodiments may provide an apparatus for exchanging heat with an extremity of a mammal and/or controlling body temperature further comprising a fluid source that is in fluid communication with a heat exchanging plenum in one of the one or more thermal exchanging units, and in which the one or more thermal exchanging units are formed from a flexible and compliant material. Alternatively, the one or more thermal exchange units may be electric pads. Additionally, the body element may comprise a first body element section and a second body element section that can be positioned to at least partially enclose the internal region by use of an enclosing clip.

Embodiments may further provide a method of exchanging heat with an extremity of a mammal to aid in the placement or advancement of a device into a vascular structure of the mammal and/or controlling body temperature in a mammal, comprising positioning an extremity of a mammal in an internal region that is formed using one or more walls of a body element, disposing one or more thermal exchanging units in proximity to a surface of the extremity that is positioned within the internal region, controlling the temperature of the one or more thermal exchange units, and/or regulating the temperature of IV fluid through use of at least one of the thermal exchange units. Methods may further comprise feeding a portion of an IV tube through an aperture in the body element. Methods may also comprise adjusting the pressure in the internal region to cause one of the one or more walls to urge at least one of the one or more thermal exchange units against the surface of the extremity. Moreover, methods may comprise sealing a portion of the body element to the extremity to enclose the internal region. Additionally, methods may comprise applying a compression force to the extremity of the mammal.

Embodiments may further provide a method of exchanging heat with an extremity of a mammal to aid in the placement or advancement of a device into a vascular structure of the mammal, comprising positioning a portion of an extremity of a mammal in an internal region of a body element, wherein the extremity is disposed in the internal region through an opening in the body element, transferring heat between the portion of the extremity disposed in the body element and a thermal exchange unit, bonding a portion of the body element to a surface of the extremity, wherein the portion of the body element comprises an aperture that surrounds a first region of the surface, and inserting a catheter into the first region through the aperture and into an artery or a vein found in the extremity.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1 is a cross-sectional view of one embodiment of an exemplary device according to one embodiment of the invention.

FIGS. 2E-2F are side cross-sectional views of a portion of an aperture formed in an exemplary device according to one embodiment of the invention.

FIG. 3A is another exemplary device with a portion of an extremity disposed and sealed therein according to one embodiment of the invention.

FIG. 3B is another exemplary device with a large portion of an extremity disposed and sealed therein according to one embodiment of the invention.

FIG. 6A is a perspective view of another exemplary device with an IV port and IV preheating section according to one embodiment of the invention.

FIG. 6C is a side cross-sectional view of an IV port formed through a portion of an exemplary device according to one embodiment of the invention.

FIG. 6D is a perspective view of another exemplary device with a heat exchanger for IV heat control according to one embodiment of the invention.

FIG. 6E is a side cross-sectional view of one embodiment of a heat exchanger for IV heat control.

FIG. 7 illustrates an exemplary manifold with one or more fittings for tubing's according to an embodiment of the invention.

DETAILED DESCRIPTION OF THE INVENTION

Figure 2A:
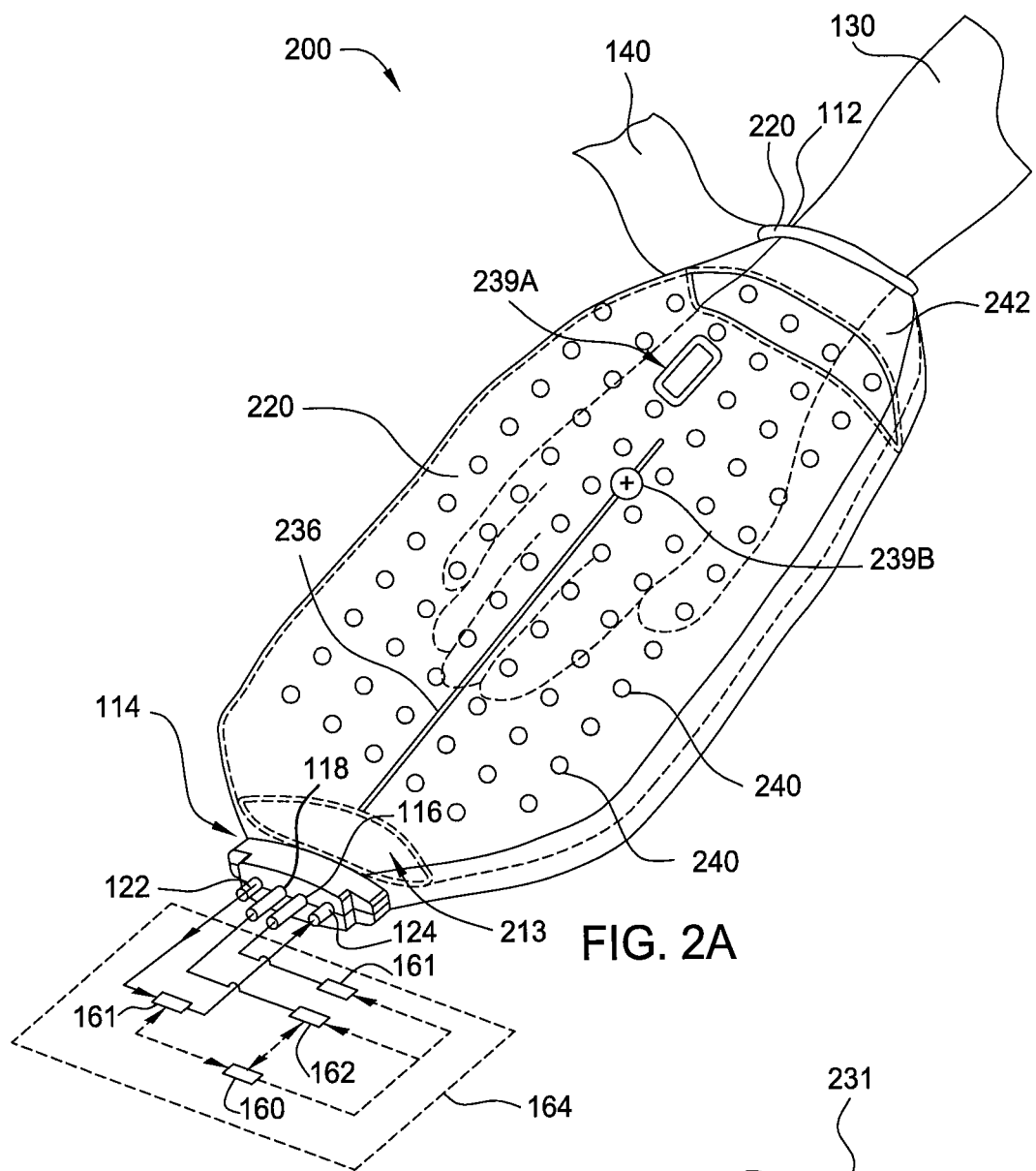
FIG. 2A is a perspective view of another exemplary device according to one embodiment of the invention.

Embodiments of the invention disclosed herein generally include methods and/or devices for increasing blood flow, controlling the vasodilatation of a patient's vascular structure, regulating the temperature of a portion of a mammal, and for improving various interventional procedures and/or therapeutic techniques. In some embodiments, the device generally includes one or more collapsible and pliant body elements, capable of expanding from a first volume into an expanded second volume so the device can receive a portion of an extremity of the mammal therein and then be reduced from the expanded second volume into a pressurized third volume, such as by applying a vacuum between the body element and extremity, to conformably enclose the portion of the extremity. The device may also include one or more access ports, or apertures, that allow access to portions of the mammal's extremity to allow interventional type medical devices, therapeutic devices, surgical devices, surgical support equipment or patient monitoring devices to have access to the extremity on which the pliant body element is disposed. The device may also be configured to allow other supporting components, which may include IV tubing or catheters, a means of accessing to a portion of the extremity positioned inside the temperature regulating device. In one configuration the device comprises flexible materials that are adapted to conform to the surface of the extremity disposed in the device when a vacuum pressure is applied to an internal region of the device.

In operation, one or more of the embodiments described herein are used to control the temperature of an extremity of a mammal by providing a heated or cooled fluid medium or electric thermal energy to one or more thermal exchange units disposed in or coupled to a pliant body element. Next, by evacuating the region in which the extremity is enclosed the contact surface area between the extremity of a mammal and the one or more thermal exchange units is increased, due to the external atmospheric pressure acting on the pliant body elements against the skin of the extremity of the mammal. The application of pressure assures that sufficient contact to improve the thermal heat transfer (heating or cooling) to the extremity of the mammal. Also, surprisingly by controlling the application of pressure to the mammal's extremity that is positioned within the enclosed region of the one or more collapsible and pliant body elements skin perfusion can be improved. The external pressure that is applied to the extremity can be adjusted to increase the blood perfusion at the skin surface of the extremity, and also improve heat transfer to the blood and rest of the body. It is believed that regulating the pressure in the region around the mammal's extremity to allow an external pressure (e.g., atmospheric pressure) or force to create a contact pressure between the device components (e.g., thermal exchange units) and the extremity of about 13.5 mmHg will provide a desirable increase of blood perfusion. It is also believed that the exposure of the skin of the extremity to a sub-atmospheric pressure environment can also help the vasodilatation of the vasculature in the mammal's extremity. The vasodilatation of the vasculature may also help to increase the thermal exchange between the one or more thermal exchange units and the mammal's extremity.

The extremity of a mammal on which the pliant body element may be disposed will desirably include regions of a mammal's body where Arteriovenous Anastomoses (AVAs) are located. These type of extremities may include an arm, a hand, a forearm, a forearm with an elbow, a hand with a wrist, a limb, a foot, a leg, a calf, an ankle and toes. Arteriovenous Anastomoses (AVAs), which are connected to arteries and veins, are specialized blood vessels located primarily in the palms and fingers of the hands, the soles and toes of the feet, the cheeks, and the ears. It is recognized that the device described herein may be adapted for use with other extremities that have vasculature structures suitable for the increasing blood flow methods described herein. Regulating the temperature of the mammal's extremity may include elevating, cooling, and/or maintaining the mammal's temperature. The mammal may be a human or other mammal. People at high risk of DVT, PE and other conditions, such as edema, wound swelling, venous stasis ulcers, diabetic wounds, decubitous ulcer, orthopedic surgery patients, coronary related interventional or therapeutic procedures, spinal cord injured individuals, among others, can benefit from the invention.

According to one or more embodiments of the invention, devices and methods are provided to intervene thermal maladies (e.g., hypothermia and hyperthermia, etc.), to regulate the temperature of the extremity of a mammal when the thermoregulatory system of the mammal is compromised (e.g., by general anesthesia, local anesthesia, trauma, post-surgery conditions, or other factors), enhance interventional or therapeutic procedures and/or to prevent deep vein thrombosis (DVT), pulmonary embolism (PE), and other diseases. The devices and methods as described herein are tested to be able to increase blood flow in the extremity of the mammal, which may include an appendage. Experiments performed on humans that have diabetes indicate that optimal pressure to increase blood flow could be about 13-14 mmHg, but that pressures between 1 and 80 mmHg, and more preferably 3 and 40 mmHg and more preferably 5 and 20 mmHg can increase blood perfusion. Pressures of approximately 14 mmHg combined with appropriate heat can increase blood flow, as a percent per minute of the volume of the appendage (in this case an arm) from a base level of between about 4% per minute to an increased level of about 8% per minute. The pressure applied to the skin by the device can be used to increase blood flow, which can be accomplished by a variety of methods including, but not limited to using atmospheric pressure to collapse a bag that has been evacuated or by pressurizing, or inflating, a cuff that encompasses a significant portion of appendage. Some results and embodiments are discussed below.

In one embodiment, a device for increasing blood flow and preventing deep vein thrombosis (DVT) is provided to a mammal's extremity by using atmospheric pressure outside the enclosed extremity to increase the surface area of the contact between the skin of the mammal's extremity and one or more thermal exchange units to improve profusion, and by regulating the temperature of the mammal's extremity by controlling the temperature of the thermal exchange units. In this case, the external atmospheric pressure is used to press the one or more thermal exchange units against the mammal's extremity to provide as much thermal exchange as possible, and increasing the blood flow of the mammal's extremity. In particular, the invention provides a non-invasive, convenient apparatus for efficiently adjusting the temperature, applying vacuum, and/or applying compression pressure or forces, to the mammal's extremity to increase blood flow, promote venous blood return, prevent clots in the veins, and prevent DV, among others.

FIG. 1 is a cross-sectional view of one embodiment of a device 100 that is used to increasing blood flow by transferring heat to a mammal's extremity. The device transfers heat to and/or from a mammal's extremity, such as an arm, a hand, a forearm, a forearm with an elbow, a hand with a wrist, a limb, a foot, a leg, a calf, an ankle, toes, etc., where AVAs are located to provide an improved and efficient control of the patients temperature, and blood flow in the extremity. FIG. 1 is a cross-sectional view of one embodiment of a device 100 having one or more thermal exchange units 120A, 120B. The device 100 includes an opening 112 formed in one or more body elements 110, which is used to enclose and receive a portion of an extremity 130 of a mammal, and one or more apertures 239, such as apertures 239A or 239B, which can allow access to the extremity. The device 100 may also contain a sealing element 140 that is attached to the opening 112, which is used to form a seal around the extremity 130. The internal region 113 of the device 100 in which the extremity 130 is enclosed can then be evacuated to allow the atmospheric pressure external to the one or more body elements 110 to urge the one or more thermal exchange units 120A, 120B against the extremity 130 to provide a desired thermal exchange. Also, by enclosing the extremity 130 the thermal environment formed around the extremity can help to improve the control of the temperature and heat exchange between thermal exchange units and the extremity.

The body element 110 is generally designed so that it will occupy a minimum amount of space, or volume, so that it can be easily and conveniently folded, stored, or shipped. The body element 110 is generally capable of being expanded from a minimized volume into an expanded volume for containing a portion of an extremity of a mammal therein. Under a pressurized condition, the volume or space of the body element 110 may be reduced from the expanded volume into a pressurized volume or space, such as a volume that conformally encloses the portion of the extremity 130. It is generally desirable to use a body element 110 that is flexible enough to allow the pressure applied to each and every portion of the extremity 130 enclosed inside the device 100 to be evenly and equally distributed.

Embodiments of the invention provide subjecting portions of an extremity of a mammal to a reduced pressure environment, preferably under vacuum or a negative pressure to increase contact surface area for thermal regulation, and adjusting the temperature of the extremity of the mammal, thereby increasing blood flow. Under a reduced pressure inside the device 100, the portions of the body element 110 are pressed against extremity 130. The pressure inside the internal region 113 of the pressurized volume of the body element 110 of the device 100 can be regulated to a level lower than atmospheric pressure, such as a pressure level of about 0 mmHg to about −80 mmHg by use of a pump 163 (e.g., mechanical pump). In another example, it is desirable to regulate the pressure in the internal region 113 to a pressure between about −10 mmHg to about −14 mmHg. In another example, it is desirable to regulate the pressure in the internal region 113 to a pressure between about −10 mmHg to about −13.5 mmHg.

The body element 110 is comprised of a collapsible and pliant material, including but not limited to, urethane, polyurethane, polypropylenes, polystyrenes, high density polyethylene's (HDPE), low density polyethylene's (LDPE), poly vinyl-chloride (PVC), rubbers, elastomers, polymeric materials, composite materials, among others. For example, the body element 110 can be made of disposable low cost materials. The collapsible and pliant material may comprise any suitable flexible material, for example, gas permeable thermoplastics, elastomeric materials, such as C-FLEX™ from Consolidated Polymer Technologies, Inc. (Largo, Fla.), DynaFlex from GLS Corporation (McHenry, Ill.), materials available from Argotec (Greenfield, Mass.), and other elastomeric materials with similar properties. The body element 110 can also be made of a biocompatible or hypo allergic material that can be sterilized. This is especially important if the device is used during surgery where sterile conditions are very important. The thickness of the collapsible and pliant material is not limited as long as it can sustain the pressurized conditions when the device 100 is used. In one example, a PVC material or a urethane material having a thickness from about 1.5 mils to about 12 mils can be used to pliantly conform to the shape and size of the portion of the extremity 130 contained therein. In general, the thickness of the collapsible and pliant material is not limited as long as it is compliant enough to substantially conform to the extremity and can sustain the desired pressurized conditions when in use.

The one or more thermal exchange units 120A, 120B can be attached to one or more portions of the body element 110 and adapted to contact the portion of the extremity 130 under pressurized conditions and to increase, reduce, or maintain the temperature of the extremity 130 received therein. The thermal exchange unit 120A, 120B can be permanently or detachably placed inside the device 100 to provide thermal exchange for the extremity 130 received therein. Examples of some exemplary thermal exchange units 120A, 120B are illustrated and further discussed in conjunction with FIG. 5. Accordingly, the materials of the body element 110 and the thermal exchange units 120A, 120B are made of a flexible material, which can be pliant and easily collapsible to conform into the shape of the extremity and securely surround and enclose the portion of the extremity 130 to provide good contact between the surfaces of the extremity 130 and the thermal exchange units 120A, 120B (or the body element 110). It is also generally desirable to assure that the thermal exchange unit(s) will not loose contact with the extremity 130 through normal jostling or positioning of the patient. Also, optimal contact and efficient thermal exchange between the thermal exchange units and the extremity 130 can be compromised when portions of the extremity 130 become arched or deformed due to the pressure differential acting on the extremity and the exterior of the device 100 when the internal region 113 is evacuated. In one embodiment, the collapsible and pliant body elements of the device helps to assure that sufficient contact between the thermal exchange units 120A, 120B and the extremity 130 is maintained if the extremity becomes arched or deforms.

The body element 110 may include one or more openings for attaching various fluid ports or pressure ports, such as a pressure port 116, a pressure sensing port 118, the fluid supply line 124, and the fluid return line 122. Accordingly, one or more thermal exchange supply lines (e.g., item 124) and one or more thermal exchange return lines (e.g., item 122) can be connected to one or more thermal sources (e.g., fluid source 161) through the one or more openings formed in the body element 110. In one embodiment, a manifold 114 may be formed or disposed on a portion of the body element 110 to provide the connections between the various external components to the device 100. A manifold 114 design that can be used with one or more embodiments described herein are further described below in conjunction with FIG. 7.

The sealing element 140 is formed on a portion of the opening 112 and is adapted to form a seal between a portion of the extremity 130 that is placed inside the internal region 113 of the body element 110 and the body element 110 to allow a negative pressure to be created in the internal region 113 by the pump 163. The sealing element 140 may be adapted to allow a pressurized volume to be formed so that an even and equal pressure is applied on each and every position for the portion of the extremity 130 of the mammal. The sealing element 140 is generally sized and used to seal the opening according to the size of the portion of the extremity 130 of the mammal. The sealing element 140 may be made of a material that is biocompatible (and therefore safe for contact with the skin of a mammal) and capable of producing an airtight seal. In one embodiment, the sealing element 140 is detachably attached to the opening 112, and may comprise a disposable sealing material that can be sterilized before use and/or is hypoallergenic to meet health and safety requirements. For example, the material of the sealing element 140 may be hydrogel, a sticky seal material, polyurethane, or urethane, such as a PS series thermoplastic polyurethane from Deerfield Urethane, Inc. The sealing element 140 may include an air permeable portion and/or made of a permeable membrane material or a breathable material to permit the flow of air. In one embodiment, the sealing element 140 may comprise a strip of releasable adhesive tape ranging from 0.5 inches to 6 inches in width, for example, a width large enough to cover the bottom of the extremity 130. The sealing element 140 is generally long enough that when wrapped end over end around the edge of the opening 112, an overlap of about 0.5 inches or larger, such as about 2 inches, is present. An example of a sealing element 140 and opening 112 configuration that may be adapted for use with one or more of the embodiments described herein is further described in the commonly assigned U.S. patent application Ser. No. 11/870, 780, filed Oct. 11, 2007, which is herein incorporated by reference in its entirety. It is recognized that the sealing element 140 is one example of a seal that may be used with the device 100, and in some cases it may be desirable not to use a seal at all. However, it is generally desirable provide a seal to reduce the leakage and thus reduce the amount of air that must be continuously removed from the apparatus during the use of the device 100.

FIG. 2A is a perspective view of another example of a device used to increase blood flow by transferring heat to a mammal's extremity, such as device 200, according to one or more embodiments of the invention. The device 200 may include a thermal exchange unit 220, one or more apertures 239, a pressure port 116, a pressure sensing line 118, a fluid supply line 124, a fluid return line 122, an opening 112 for the extremity to be enclosed therein, and a sealing element 140, which are similar to the components discussed above. A manifold 114 may be formed for providing the connection between the various fluid ports or pressure ports, such as the pressure port 116, the pressure sensing line 118, the fluid supply line 124, and the fluid return line 122, and other external components, which is further discussed below in conjunction with FIG. 7.

In one embodiment, the thermal exchange unit 220 is permanently attached to the device 200 and composed of a collapsible and pliant material, including but not limited to, urethane, polyurethane, elastomers, polypropylenes, polystyrenes, high density polyethylene's (HDPE), low density polyethylene's (LDPE), poly(vinyl chloride), rubbers, polymeric materials, composite materials, among others. The thermal exchange unit 220 is generally designed to allow a fluid medium to be delivered there through to exchange heat with an extremity. As a result, there is no need for a separate body element (see item 110 in FIG. 1), and thus the thermal exchange unit and body element can be considered one integral piece. In this case, the thermal exchange unit 220 can be used to enclose the extremity 130 by forming an internal region 213 that can be evacuated. In addition, the body of the thermal exchange unit 220 is capable of forming a minimized volume for folding, storage, and/or shipping. The space enclosed by the thermal exchange unit 220, or internal region 213, can also be expanded so that the extremity 130 can be disposed therein. The internal volume 213 of the thermal exchange unit 220 can be reduced under a pressurized condition to conformably apply even and equal pressure on the portion of the extremity 130 disposed inside the device 200.

The thickness of the material for the thermal exchange unit 220 is not limited as long as it is compliant enough to substantially conform to the extremity and can sustain the pressurized conditions when the device 200 is used and the fluid medium can be delivered therein. For example, a urethane material having a thickness of from about 1.5 mils to about 12 mils can be used to pliantly conform to the shape and size of the portion of the extremity 130 contained therein. Another possible material may include NTT-6000, which is a polyether polyurethane manufactured using USP Class V1 compliant materials. Examples of thermal exchange units 220 and body elements 110 are further described in U.S. patent application Ser. No. 11/830,486, filed Jul. 30, 2007, which is incorporated by reference herein.

Figure 2B:
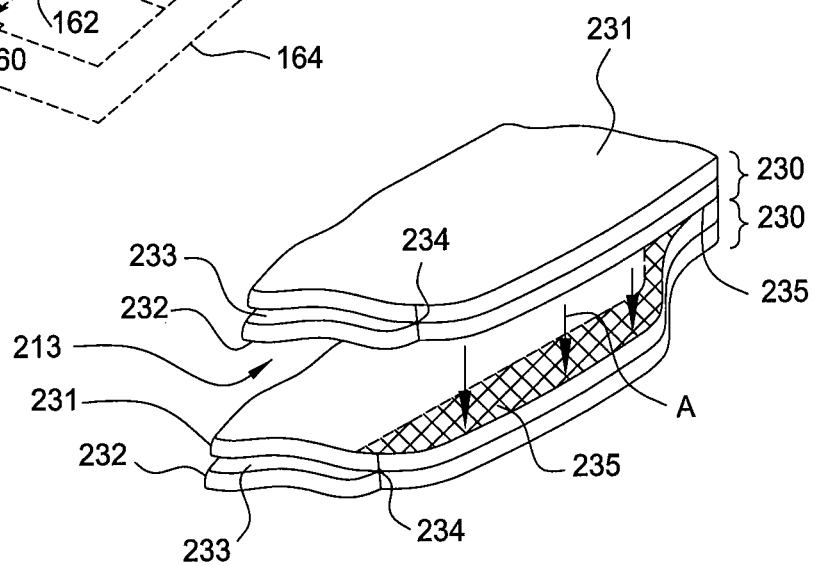
FIG. 2B is a close-up partial exploded view of a portion of the thermal exchange unit according to one embodiment of the invention.

In one embodiment, as shown in FIG. 2B, the thermal exchange unit 220 is formed by bonding or sealing two layers (e.g., layers 231 and 232) of a collapsible and pliant material together to form a composite element 230 having a fluid plenum 233 formed between the bonded and sealed layers to allow a heat exchanging fluid to be delivered from the fluid source 161 there through. FIG. 2B is a partially exploded cross-sectional view of a portion of the thermal exchange unit 220 according to an embodiment of the invention. The layers 231 and 232 can be sealed (e.g., seal 234) by use of a heat sealing, gluing, or other conventional compliant layer bonding technique. Then two or more composite elements 230 can then be bonded together (see "A" in FIG. 2B) at a sealing region 235, using a heat sealing, gluing, or other conventional technique, to form the internal region 213 in which the extremity 130 can be placed. The internal region 213 is thus also isolated or separate from the fluid plenum 233 formed between the bonded and sealed layers. The layers 231 and 231 may composed of a collapsible and pliant material, including but not limited to, urethane, polyurethane, polypropylenes, polystyrenes, high density polyethylene's (HDPE), low density polyethylene's (LDPE), poly(vinyl chloride), rubbers, elastomers, polymeric materials, composite materials, among others.

In one embodiment, a plurality of dimples 240 are formed between the layers 231 and 231 to form a stronger composite element 230 that will not dramatically expand when a heat exchanging fluid is delivered from a fluid source 161 to the thermal exchange unit 220. In one embodiment, a separating feature 236 is formed through a region of the composite element 230 to allow fluid delivered from the fluid supply line 124 to flow through the fluid plenum 233 and around the separating feature 236 before the fluid exits the thermal exchanging unit 220 and enters the fluid return line 122. The separating feature 236 may be formed by RF welding, thermal sealing, gluing, or bonding the layers 231 and 231 together. In one embodiment, a composite element 230 is formed on either side, or wraps around, the extremity 130 in the device 200 to provide improved thermal contact and heat exchanging properties.

Figure 2C:
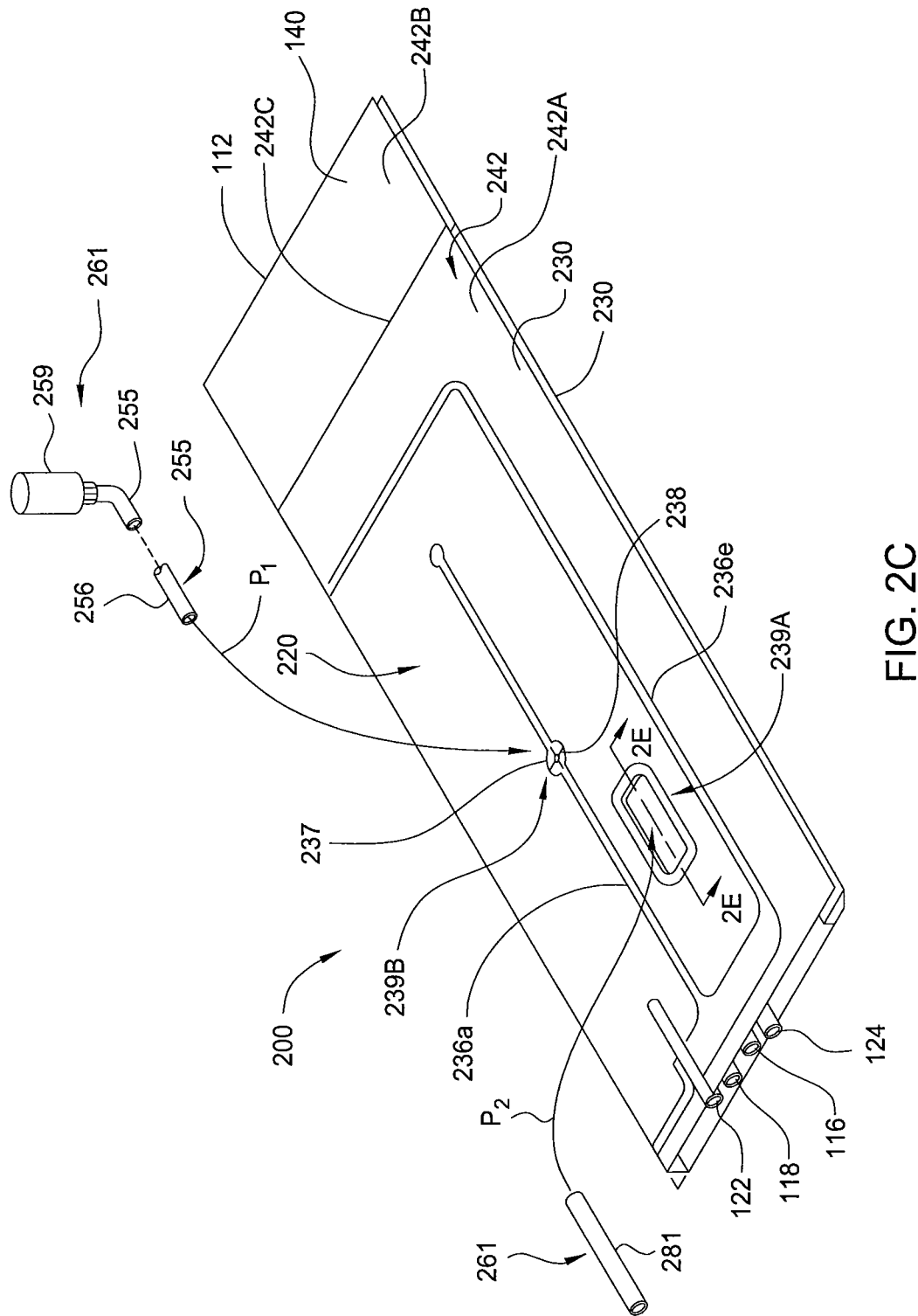
FIG. 2C is a perspective view of another exemplary device having at least one aperture formed therein according to one embodiment of the invention.
Figure 2D:
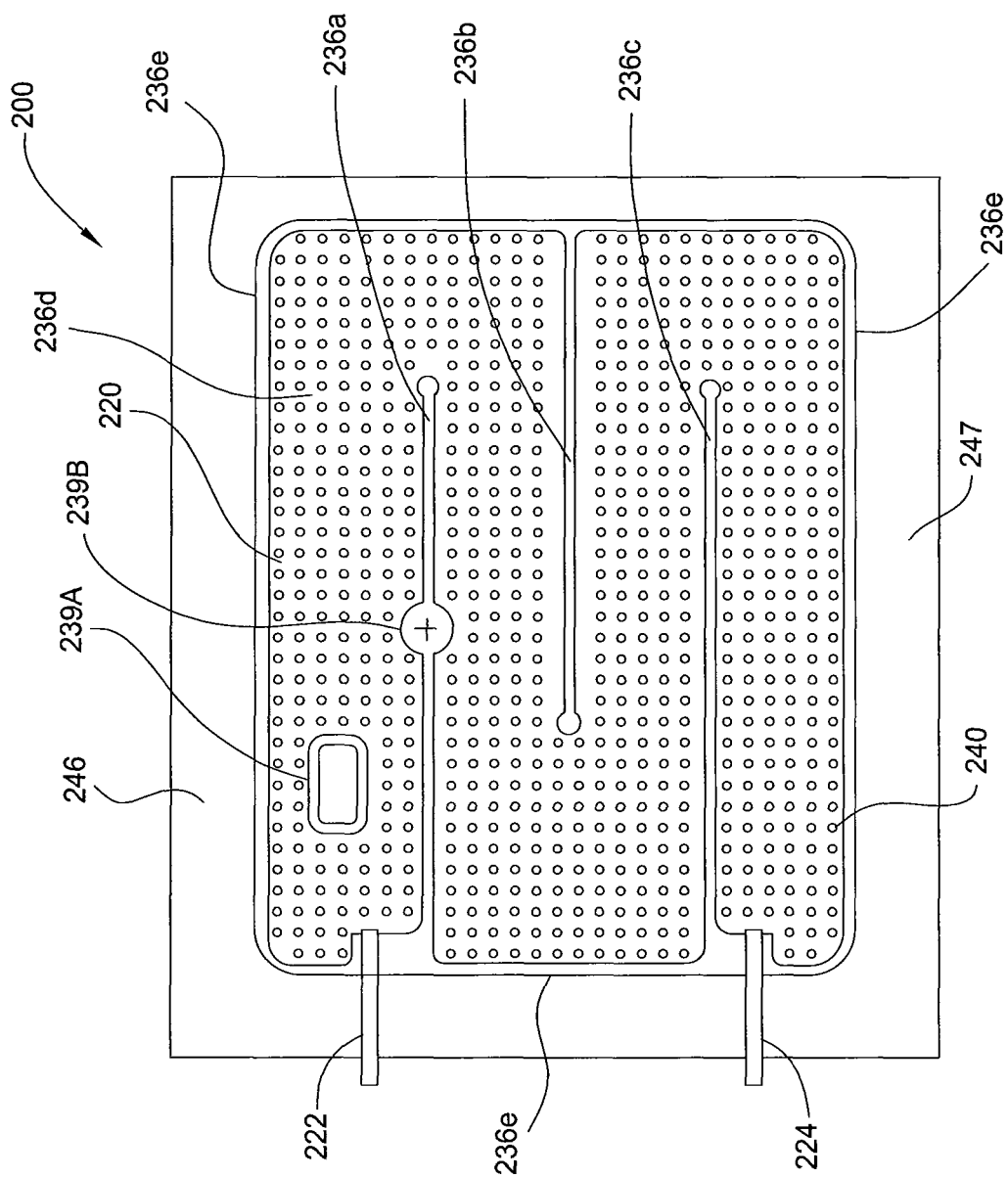
FIG. 2D is a perspective view of another exemplary device having at least one aperture formed therein according to one embodiment of the invention.

In one configuration, the device 200 may be formed into a sleeve, such as illustrated in FIG. 2C, by folding the bonded layers over and coupling the bonded layers to form the internal region 213 in which the extremity 130 can be disposed. The device 200 shown in FIG. 2C generally illustrate one configuration of the device 200 shown in FIG. 2A that is formed by bonding regions 246 and 247 (FIG. 2D) together to enclose the internal region 213. FIG. 2D illustrates an unfolded and unsealed version of the thermal exchange unit 220 shown in FIG. 2C, which has segmented regions that are adapted to improve the flow of a heat transfer fluid through the thermal exchange unit 220 to improve the heat transfer between the extremity 130 and the thermal exchange unit 220. In the configuration illustrated in FIG. 2D, fluid may enter through fluid supply line 124, flow in a path around dimples 240 and a plurality of separating features 236a, 236b and 236c within the fluid flow region 236d, which is enclosed by the outer wall(s) 236e, and exit through fluid return line 122. Dimples 240 and separating features 236a, 236b and 236c may be formed by RF welding two layers (e.g., layers 231 and 232) of a material together, such as a discussed above in conjunction with FIGS. 2A-2B.

FIGS. 2C-2F also illustrate embodiments of the device 200 that are adapted for use with interventional procedure medical devices, therapeutic procedure devices, surgical support equipment or patient monitoring devices that can be attached to a patient, such as an IV, catheter, thermometer, or oximetry device. In one example, a catheter device may be inserted into the extremity 130 (FIG. 2A) through an aperture 239, such as aperture 239A or aperture 239B shown in FIGS. 2C-2D, formed within the device 200. In another example, the IV may be attached to the extremity 130, which may be at least partially disposed within the device 200. At least one flow path for IV fluid may be positioned in proximity to the one or more thermal exchange units disposed in the device 200, such that heat may be transferred to or from the IV fluid. In one example, the flow path comprises an IV tube. An example of device 200 that is adapted for use with an IV tube is further described in the provisional patent application Ser. No. 61/293,564, filed Jan. 8, 2010, which is herein incorporated by reference in its entirety.

Referring to FIG. 2C, in one embodiment, a device 261, such as an interventional procedure medical device, therapeutic medical device, surgical device, surgical support equipment or patient monitoring device, such as an IV tube (e.g., IV tube 255 in FIG. 2C) may be inserted into an aperture 239 formed in the device 200. The one or more apertures 239 are provided to allow access to an extremity 130 (not shown in FIG. 2C) positioned in the internal region 213 of the device 200 through the layers 231 and 232 (FIGS. 2B and 2E-2F) used to form the composite element 230. In one example, a first aperture 239B may be provided in a location suitable for an IV tube, and a second aperture 239A may be provided in a location suitable for allowing a catheter, second IV tube, and/or other supporting elements to reach the patient. Apertures may also be provided for other purposes as well, such as access to the extremity during an interventional, therapeutic or surgical procedure or other useful purposes. In one configuration, which is discussed further below, a device 261, such as a catheter 281, is inserted into a vein or an artery in the extremity 130 of a patient through an aperture 239A (see path "$P_2$" in FIG. 2C). In another configuration, a device 261, such as an IV tube 255, may be inserted into a vein or an artery in the extremity 130 through a port 237 (see path "P$_1$" in FIG. 2C) formed in the device 200.

In one embodiment of the device 200, a separating feature 236 may be formed, which provides a stable location for the port 237 formed in the aperture 239B to provide access to the patient's extremity. The separating feature 236 may be a fused or bonded region formed in a composite element 230. The separating feature 236 can be formed, for example, by welding the layers 231 and 232 together and adding scoring marks 238 to allow a device 261 to access the extremity and/or internal region 213 of the device 200. In one configuration, the port 237 is centrally located and is able to form a seal between the components found in the composite element 230 and the outer wall 256 of the device 261, such as a catheter 281 or IV tubing 255 (FIG. 2C). In one embodiment, as illustrated in FIGS. 2C-2D, the separating features 236 also forms a path for the heat exchange fluid to flow through the fluid plenum 233 (FIG. 2B) formed in the device 200. Device 200 may be manufactured from a PVC pad that is RF welded and folded over along an edge. Additionally, body element 242 may comprise a sealing element 140, as discussed above. In one configuration, the body element 242 comprises a central body region 242A (FIG. 2C) and sealing element region 242B (FIG. 2C) that are bonded or joined together at a connection region 242C. In one example, the central body region 242A comprises a compliant material, such as poly vinylchloride (PVC), and the sealing element region 242B comprises a compliant material, such as a urethane or polyurethane material, that are joined together by a RF welding, thermal bonding or similar attachment technique at the connection region 242C. It is believed that by use of a more rugged complaint material in the central body region 242A (e.g., 0.005-0.012 inch thick PVC material) and a more flexible or elastic material in the sealing element region 242B (e.g., 0.001-0.005 inch thick urethane material) will help form a robust device that forms a better seal to the patient's extremity 130 at the sealing element region 242B, and prevent this portion of the device from acting as a tourniquet when the internal region 213 is evacuated.

FIGS. 3A and 3B illustrate two different configurations of a device 100 or a device 200 that have a portion of an extremity 130 disposed and sealed therein. In one configuration, an extremity 130, such as a hand, is enclosed in a device (e.g., reference numeral 400A (FIG. 3A)) that is shaped like a mitten or a glove. In this configuration, the one or more thermal exchange units 420 are sized to heat the desired area of the extremity 130 that is positioned within the body element 410, which may be similar to the body element 210 discussed above. The internal region 413 of the device 400A can be evacuated and the thermal exchange unit(s) 420 can be temperature regulated by use of the controller 160, fluid source 161, vacuum sensor 162 an/or a pump 163, which is schematically illustrated in FIG. 3A.

In another configuration, as shown in FIG. 3B, the extremity 130 enclosed in a device 400B may be a large portion of an arm, or other appendage. The device 400B can be shaped like an elongated glove to conformably enclose the arm, and may comprise elements similar to the elements found in device 400A. The increased surface area of the body enclosed and temperature controlled by use of the thermal exchange unit(s) 420 shown in FIG. 3B versus FIG. 3A may be useful to help more rapidly and/or easily control the subjects body temperature during use. While only a single thermal exchange unit 420 is shown in FIGS. 3A and 3B, this configuration is not intended to be limiting to the scope of the invention, and thus two or more thermal exchange units 420 may be positioned around various parts of the extremity 130 to improve perfusion.

Figure 4:
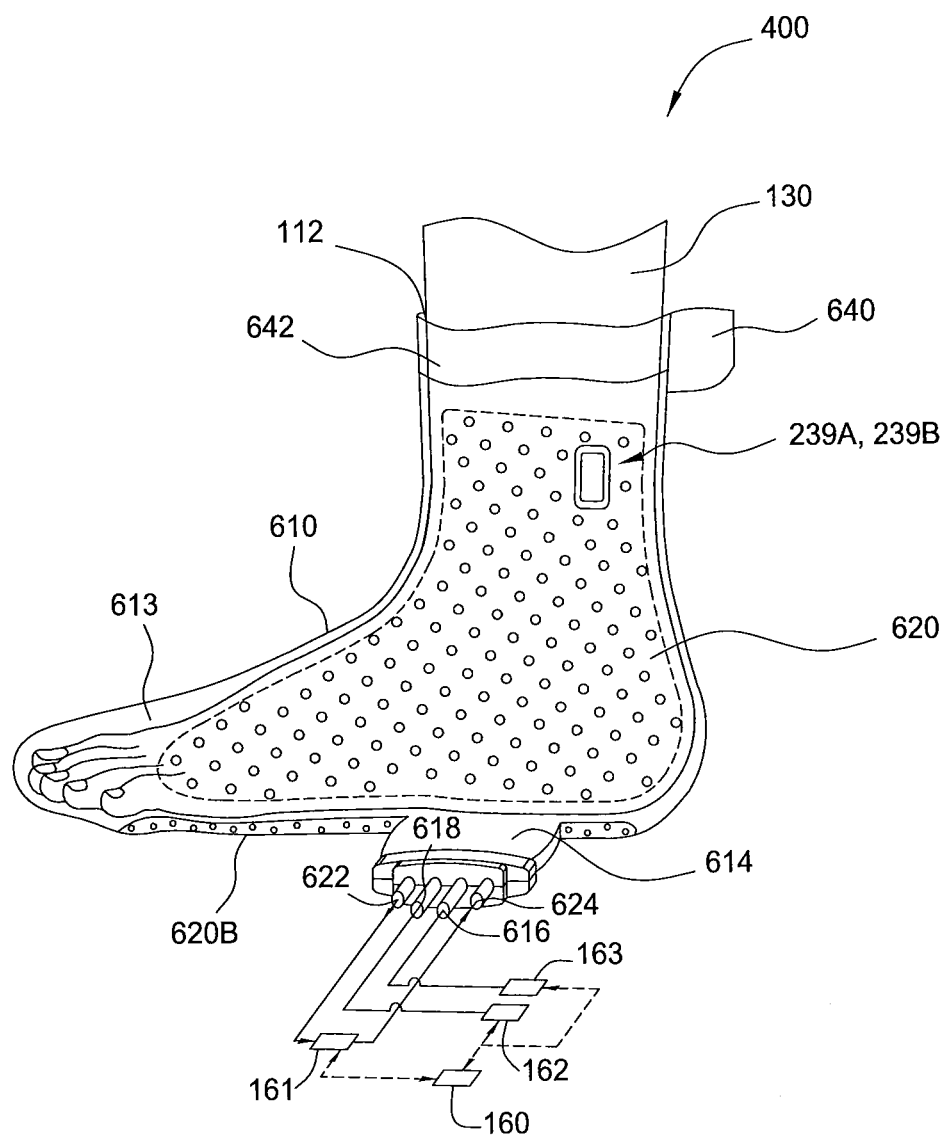
FIG. 4 is a side view of an exemplary lower extremity device according to one embodiment of the invention.

FIG. 4 is a side view of one example of a device 600, which may be used to increase blood flow and control the temperature of a lower extremity of a mammal, such as a foot, according to one embodiment of the invention. The device 600 includes a body element 610 for forming a pressurized volume, one or more thermal exchange units, such as thermal exchange units 620 positioned on various sides/portions of the extremity 130, the opening 112 for containing the extremity 130, and a sealing element 640 attached to the opening 112. An additional sealing element, such as a sealing element 642, may be used to adequately seal the extremity 130 within an internal region 613 of the device 600. In one embodiment, a thermal exchange unit 620 is permanently attached to the device 600 and composed of a collapsible and pliant material, similar to the configuration discussed above in conjunction with FIGS. 2A-2B. The thermal exchange unit 620 is generally designed to allow a fluid medium to be delivered there through to exchange heat with an extremity. In one embodiment, the devices 600 may include an aperture 239 (e.g., apertures 239A, 239B shown in FIG. 2C) that are adapted to allow access to a portion of the lower extremity so that interventional type medical devices, therapeutic type medical devices, or patient monitoring devices can be attached to a patient there through.

Heat Transfer and Thermal Control Features

In general, a thermal-exchange fluid medium, such as heated fluid, heated air, cooled fluid, or cooled air, etc., can be provided from a fluid source 161 into the thermal exchange units 120A, 120B, 220, 420 or 620 via one or more fluid supply lines 124 and out of the device 100, 200, 400 via one or more fluid return lines 122. The temperature of the one or more thermal exchange units positioned in the device 100 may also be controlled by use of an electric pad, fluid type heat exchanging device, or any other suitable thermal exchange units, that are used individually or in combination. Thermal energy can be transferred from the thermal exchange unit to the extremity 130 during heating or from the extremity 130 to the one or more thermal exchange units during the process of cooling the extremity 130. For example, the thermal exchange units may be a fluid heating pad having, for example, heated water delivered there through using a recirculation type heat exchanging system. As another example, the thermal exchange units may be a pad having chemicals therein for heating or cooling. Alternatively, the thermal exchange units may include an electric pad, as described in detail in co-pending U.S. provisional patent application Ser. No. 60/821,201, filed Aug. 2, 2006, and U.S. patent application Ser. No. 11/830,486, filed Jul. 30, 2007, which are both incorporated by reference herein.

Figure 5:
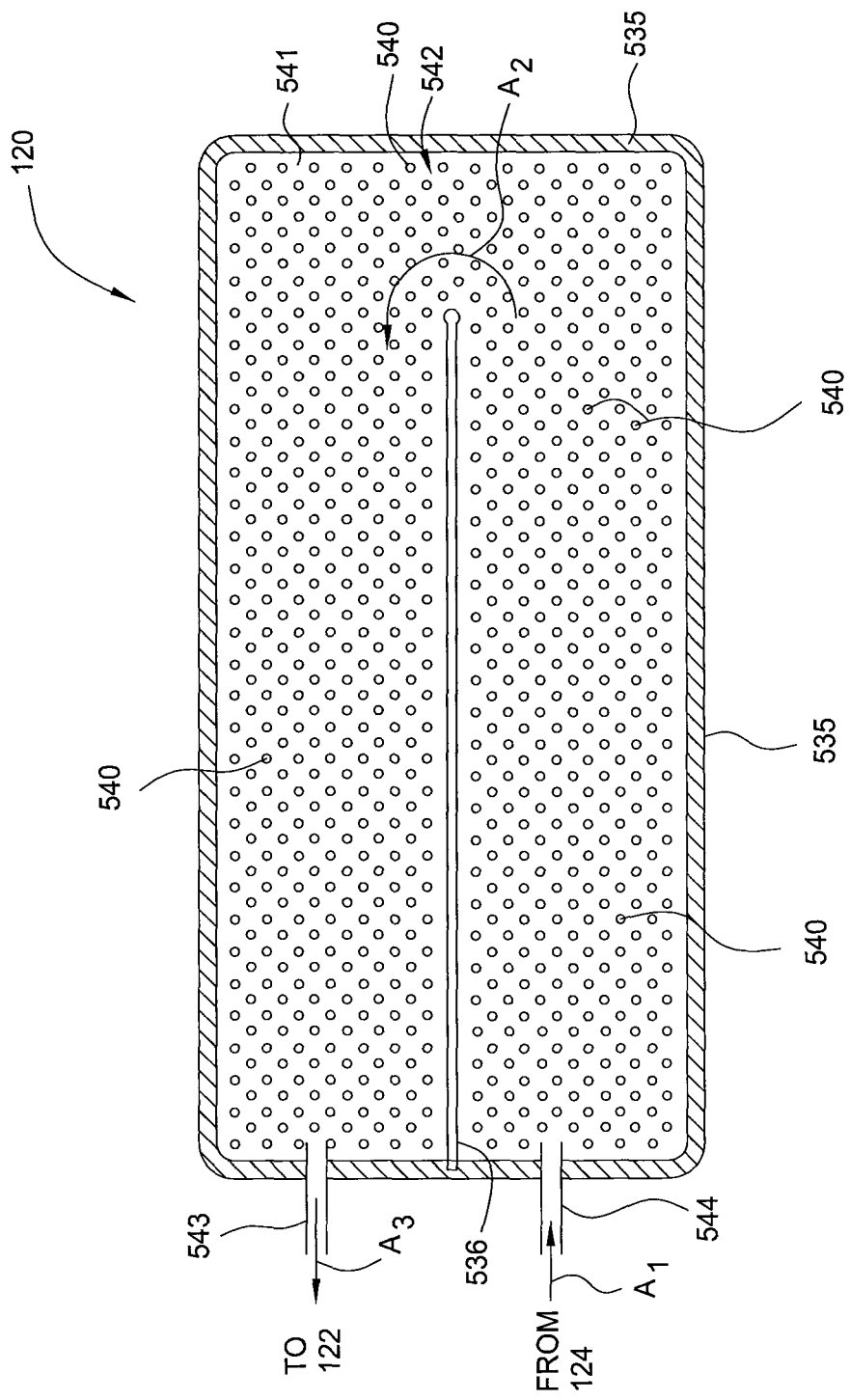
FIG. 5 illustrates one example of a thermal exchange unit according to one embodiment of the invention.

FIG. 5 illustrates one configuration of a thermal exchange unit 120A, 120B, 420 or 620, or part of a thermal exchange unit 220, that are formed using two layers of a compliant material 541 that are sealed at the edge region 535 by use of an RF welding, thermal sealing, gluing or other bonding process to form a sealed main body 542. The main body 542 may have an inlet port 544 and an outlet port 543 that are in fluid communication with the fluid source 161, and the fluid supply line 124 and fluid return line 122, respectively. The region formed between the two layers of the compliant material 541 is thus used as a fluid plenum that can receive (see arrow A$_1$) and then exhaust (see arrow A$_3$) the thermal fluid medium from the fluid source 161. In one embodiment, a separating feature 536 is formed in the thermal exchange unit to separate the fluid delivered into the inlet port 544 and the outlet port 543, and thus allow the thermal exchanging fluid to follow a desirable path through fluid plenum to optimize and/or improve efficiency of the heat transfer process. In one example, the fluid flow path sequentially follows the arrows $A_1$, $A_2$ and $A_3$. The separating feature 536 can be formed in the sealed main body 542 by bonding the two layers of the compliant material 541 together. In one embodiment, the thermal exchange unit(s) may be formed from a pliant material, including but not limited to, urethane, polyurethane, polypropylenes, polystyrenes, high density polyethylene's (HDPE), low density polyethylene's (LDPE), poly(vinyl chloride), rubbers, elastomers, polymeric materials, or composite materials. In one embodiment, the surface of contact between the thermal exchanging units (e.g., reference numerals 120A, 120B, 220, 620) and the skin of the extremity is between about 30 in$^2$ (e.g., 0.019 m$^2$) and about 410 in$^2$ (e.g., 0.264 m$^2$). In another embodiment, the surface of contact between the thermal exchanging units and the skin of the extremity is less than about 800 in$^2$ (e.g., 0.516 m$^2$).

The devices illustrated in FIGS. 1-4 will generally include a control system 164 that contains a controller 160 that is connected to various parts of the device, including the pump 163 and vacuum sensor 162 connected to one or more of the pressure ports, the fluid source 161 connected to one or more of the fluid lines connected to the one or more thermal exchange units. The controller 160 may be adapted to regulate the functions and process performed by the device, including adjusting the fluid flow in and out of the thermal exchange units, regulating the temperature of the thermal exchange units, monitoring the pressure level inside the device via one or more vacuum sensors 162, adjusting the pump 163 speed and the vacuum level inside the device 100, and monitoring the temperature of the extremity 130 received therein, among others. In one embodiment, the devices described herein may include an in-use sensor indicating that the device is in use (e.g., vacuum switch). In addition, the in-use sensor and/or controller 160 may indicate how many times the devices have been used.

According to an embodiment of the invention, the device can also be used in combination with a mechanical compression device or a pressurized compression device to help pump blood through the patient's body. Alternatively, the device 100 can itself be modified to include one or more pressure-applying gas plenums positioned within or attached to the body element in order to apply a compression force or positive gas pressure on the extremity 130 of a mammal, in addition to controlling the extremities temperature by delivering a thermally controlled fluid to the one or more fluid exchange units that are in contact with the extremity.

Interventional Procedure, Therapeutic Procedure and Other Support Devices

In one configuration, as discussed in conjunction with FIG. 2C, a catheter 281 can be inserted into a vein or an artery in the extremity 130 through the aperture 239A (see path "$P_2$") formed in the device 200. FIGS. 2E-2F are side cross-sectional views of an aperture 239A formed by sectioning the device 200, shown in FIG. 2C, along the section line 2E-2E. The aperture 239A generally comprises a seal region 297, a release liner 296 and a bonding material 295 disposed between the seal region 297 and the release liner 296. The seal region 297 surrounds the aperture 239 and is configured to sealably bond the layers 231 and 232 together to prevent any heat exchanging fluid from leaking from the fluid plenum 233 into the aperture 239. When an extremity 130 is inserted into the internal region 213 of the device 200 the aperture 239A portion of device 200 is brought near the surface 130A of the extremity 130, so that it can then be bonded to the extremity of the patient in a subsequent step.

FIG. 2F is a side cross-sectional view of an aperture 239A that has been affixed to the surface of the extremity 130 so that the internal region 213 is isolated from the external environment 299 outside of the device 200. As illustrated in FIG. 2F, after removing the release liner 296 through the aperture 239A, a surface 295A of the bonding material 295 is urged against a portion of the extremity 130 to form a seal there between. In this configuration, the internal region 213, which may be evacuated to a negative pressure during operation of the device 200, is isolated from the external environment 299 by the seal formed between seal region 297 of the device 200 and the extremity 130 by the bonding material 295. Thus, a desired medical device, such as a catheter, can be directly inserted into the exposed portion 130B of the extremity 130 without affecting the pressure in the internal region 213.

In one embodiment, the aperture 239A comprises an oval opening (e.g., 100 mm×50 mm) and the bonding material 295 comprises a band of hydrogel material that has a desired width (e.g., 10 mm) to form a seal. The release liner 296 is generally sized to prevent the bonding material 295 from coming into contact with the extremity 130 prior to the aperture being affixed to the extremity 130. The release liner 296, which comprises a plastic or paper material, may also contain a pull tab (not shown) to allow it to be easily removed from the device 200 prior to the bonding material 295 being placed in contact with the surface of the extremity 130.

One skilled in the art will appreciate that while FIGS. 2E, 2F and 6C illustrate devices that have an aperture 239A, or an aperture 239B, formed through both layers 231 and 232 of the device, this configuration is not intended to limiting to the scope of the invention, since an aperture 239A, 239B may also be formed through only a single layer 231 or 232 in areas of the device that are only a single layer thick without deviating from the scope of the invention described herein.

It is believed that by the use of one or more of the embodiments described herein, significant benefits can be achieved that allow various interventional and/or therapeutic procedures to be more easily performed, and post-operative patient recovery times and complication can be reduced. It is believed that interventional procedures and therapeutic techniques that require access to the vascular structure, such as veins or arteries, of a patient can be improved by the transfer of heat to the extremity, which thus improves the vasodilatation and relaxation of arterial wall musculature in the extremity and the rest of the patient. In one example, doctors may perform tests and other procedures to diagnose and treat various coronary artery disease. These tests often involve inserting a catheter through an artery or vein in a leg or arm and then into the heart. The term catheter as used herein could be any medical device used for accessing an artery or vein in a therapeutic or interventional procedure, and may include a radial artery catheter, IV catheter, PTCA catheter, imaging catheter, stent catheter, or other similar device. These procedures may also include, for example, angioplasty procedures and/or the placement of stents inside of a vessel. Typically, doctors usually gain access to the heart by inserting a catheter in the femoral artery. The femoral artery is a major artery in your groin area. While this technique is the most popular method, femoral artery access has many common problems, such as bleeding at the insertion site and possible nerve damage. Also, the femoral artery type procedures require the patient to lie very still for many hours after the procedure has been completed to make sure that the insertion site does not start to bleed again.

To resolve these problems, doctors have started to use the radial artery, which is an artery in your wrist, to gain access to the heart. Since the radial artery is smaller than the femoral artery, it is much easier to apply direct pressure to the puncture site to stop the bleeding at the end of the interventional or therapeutic procedure. Generally, insertion into the radial artery does not cause as much discomfort during the interventional or therapeutic procedure, and allows many patients to move about right after their procedure. Unfortunately, not all patients can have their procedure done through the radial artery, since the patient must have good blood supply to their hands, through both the radial artery and the ulnar artery. The blood supply from both arteries has to be good just in case the radial artery becomes occluded, thus requiring the ulnar artery to supply sufficient blood to the hand.

Therefore, by use of the various embodiments of the invention described herein one can relax the arterial wall musculature, thus increasing the effective size of the arteries in the arm during an interventional or therapeutic procedure, including the radial artery, to allow improved access to the heart. Generally, a device 200 can be positioned over a portion of an arm to transfer heat to the arm of the patient, while access to the radial artery in the arm is allowed through the aperture 239 formed in the device.

Referring to FIGS. 3A and 3B, in one embodiment, a device, such as device 400A (FIG. 3A) and device 400B (FIG. 3B), is positioned over a portion of an arm and sealed thereon by use of a sealing element 140, as discussed above. In one configuration, the device 400A is positioned to enclose the hand of a patient, and an aperture 239A is positioned and sealed to a portion of the arm that is over a portion of the radial artery. In another configuration, the device 400B is configured to enclose a large portion of an arm, and allow access to the radial artery through an aperture 239A positioned thereover. In either configuration, the one or more thermal exchange units 420 are sized to control the temperature of a desired area of the extremity 130, and also allow access to the radial artery through the aperture 239A. The internal region 413, which is similar to the internal region 113 or 213 shown in FIGS. 1 and 2A-2F, can be evacuated and the thermal exchange unit(s) 420 can be temperature regulated by use of the controller 160, fluid source 161, vacuum sensor 162 an/or a pump 163 to control the vasodilatation in the mammal's extremity.

Therefore, various embodiments described herein can be used to enhance the luminous size of arteries or veins, and relax of the arterial wall musculature to prevent or reduce arterial spasms during a therapeutic or an interventional procedure, to thus improve access to various portions of a patient's circulatory system, such as the heart. It is believed that the use of the embodiments described herein to cause dilation and/or relaxation of the vessels during a interventional or therapeutic procedure will also increase the number of patients that can benefit from the use of this type of interventional or therapeutic procedure, due to prior limitations due to the size of the arteries or veins in their extremity, such as the radial or ulnar arteries. It is also believed that the use of the devices described herein will improve the patient's recovery time.

IV Tubing Device Configurations

Figure 6B:
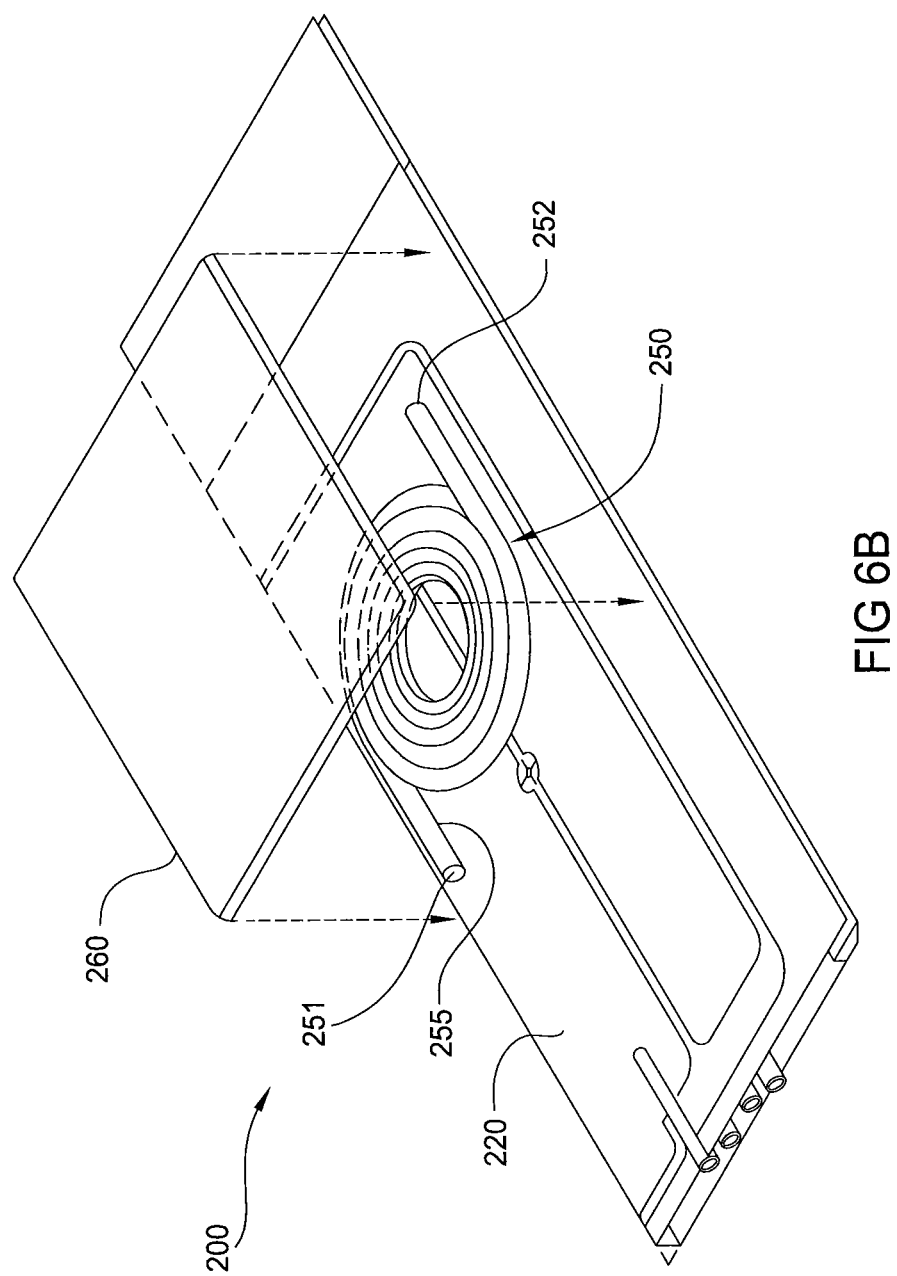
FIG. 6B is a perspective view of another exemplary device with IV preheating section according to one embodiment of the invention.

FIGS. 6A-6F illustrate embodiments of the device 200 that are adapted for use with IV related components. In one example, an IV may be attached to the extremity 130 through an aperture 239B formed within the device 200. In one configuration, at least one flow path for IV fluid may be positioned in proximity to the one or more thermal exchange units disposed in the device 200, such that heat may be transferred to or from the IV fluid. In some embodiments, the temperature of IV fluid may be regulated by a device that is also regulating the temperature of the patient or portion of the patient. For example, IV tubing set 250 may be heated by a heating pad that is also heating the patient or portion of a patient by exchanging heat with their skin. FIG. 6A illustrates an embodiment of a device 200 in which an IV tubing set 250 is positioned proximate to thermal exchange unit 220. FIG. 6B is an isometric view of a device 200 that illustrates a configuration in which the IV tubing set 250 is affixed to a portion of the thermal exchange unit 220 by use of an adhesive sheet 260 that is placed over IV tubing set 250, and possibly the port 237. FIG. 6C is a side cross-sectional view of the device 200 illustrating an IV tube 255 positioned through the port 237 to access a vein or artery of patient's extremity 130.

Referring to FIG. 2C, in one configuration, a device 261, such as an IV tube 255, may be inserted into a vein or an artery in the extremity 130 through a port 237 (see path "$P_1$" in FIG. 2C) formed in the device 200. It is to be understood that access to the extremity 130 may be desirable for other purposes, such as interventional and therapeutic procedures and/or other vascular access needs. As discussed above, in some cases, a separating feature 236 may be formed within the device 200, which provides a stable location for the port 237 formed in the aperture 239B to provide access to the patient's extremity. In one configuration, the port 237 is centrally located and is able to form a seal between the components found in the composite element 230 and the outer wall 256 of the device 261, such as the IV tubing 255. In one configuration, the internal region 213 is isolated from the external environment 299 outside of the device 200 by the seal formed between the outer wall 256 of the device 261 and the device's material found at the port 237. In one configuration, additional sealing materials may be used to form a seal between the outer wall 256 of the device 261 and an opening created by the port 237. For example, surgical tape may be placed over the outer wall 256 of the IV tube 255 and the surface of the layer 231, in which the port 237 is formed through, after an IV tube is inserted through the port 237. The use of an additional sealing material can help reduce the leakage of air into the internal region 213 through any gap formed between the outer wall 256 of the IV tubing 255 and the layers 231 and 232 in the composite element 230 when a vacuum is created in the internal region 213 by the pump 163. In general, it is desirable to form the port 237 so that any gap formed between the outer wall 256 and the layers 231, 232 is minimized to prevent the need for any additional sealing material.

Device 200 may also be used to regulate the temperature of IV fluids delivered to or from the body of the mammal through the IV tubing. For example, the heat exchanging fluid used in device 200 may also be used to exchange heat "Q" (FIG. 6C) with a fluid "F" disposed in an IV tube 255. In one embodiment, the IV tube 255 is coupled to a fluid delivery device 258, such as a tube or needle, which is in fluid communication with a vein or artery of patient's extremity 130. In one embodiment, the IV tubing set 250 is positioned so that it is in thermal contact with portions of a thermal exchange unit 220 to allow energy to be exchanged between the IV tubing 255 in the IV tubing set 250 and the heat exchanging fluid flowing through the thermal exchange unit 220. IV tubing set 250 has an outlet 251, which may be inserted into port 237, or is connected to a fluid delivery device 258 that extends through the port 237 and is in fluid communication with a vein or artery of patient's extremity 130. An inlet 252 portion of the IV tubing set 250 may be in fluid connection with an IV fluid delivery device, such as a drip bag 259 (FIG. 2C). In FIG. 6A, the IV tubing set 250 may be attached to thermal exchange unit 220 by heat staking, thermal bonding or other conventional bonding or welding techniques. In one embodiment, the tubing 255 may be formed from a plastic or elastomeric material. In one example, the tubing 255 is made from a material used to from the heat exchanging units 120 or layers 231, 232, as described herein.

While the IV tubing set 250 illustrated in FIG. 6A contains a coil of tubing 255, other fluid transferring configurations may also be used to warm or cool the IV fluid delivered to or from the patient. In one configuration, the IV tubing set 250 is positioned proximate to the flowing heat exchanging fluid to exchange heat therewith and has a desired length so that the fluid in the IV can reach a desired temperature before it reaches the extremity of the patient. In one embodiment, at least a portion of the IV tubing 255 passes within the fluid plenum 233 (FIG. 2B) to improve the thermal transfer between the heat exchanging fluid and the IV fluid. In one embodiment, manifold 114 (shown in FIG. 2A) could be made with an IV tubing port, and additional tubing could be provided inside the fluid plenum 233.

In one embodiment, the manifold 114 (FIG. 2A) may contain an IV tubing port (not shown in FIG. 2A) that could be connected at one end to an IV delivery device (e.g., IV drip bag 259 (FIG. 2C)), and at the other end to additional tubing found inside the internal region 213 of the device 200 for connection to the patient's extremity 130. In this configuration, the IV tubing 255 can be easily connected to the patient via the additional tubing found inside the internal region 213, and the IV delivery device can be easily connected to the manifold 114 using the attached tubing 255.

In FIG. 6B, an adhesive sheet 260 is placed over IV tubing set 250 and port 237. Adhesive sheet 260 may hold IV tubing set 250 against the thermal exchange unit 220. Adhesive sheet 260 may also provide a seal to cover any gaps between the outer wall 256 of the tubing 255 and the port 237. A preferred material for adhesive sheet 260 is Tegaderm® tape available from 3M. Adhesive sheet 260 may also comprise strips of tape, such as surgical tape. Embodiments may also provide a pocket for receiving IV tubing set 250.

Additionally, the IV tubing set 250 may be sterilized. In some embodiments, the IV tubing set 250 may be sterilized and attached to device 200. Other components of device 200, such as the layers 231 and 232 may either not be sterilized or may not be sterilized to the same extent as IV tubing set 250, thus reducing the equipment cost of the formed device while assuring that the patient's well being is maintained.

The temperature of the IV fluid may also be regulated by use of an external heat exchanging device, such as a heat exchanger 270 shown in FIG. 6D. FIG. 6D illustrates some embodiments, in which a tubing set 275 is provided from the control system 164 to the heat exchanger 270. Tubing set 275 may be configured and/or provide a means through which connections can be made to the pressure port 116, the pressure sensing line 118, the fluid supply line 124 and the fluid return line 122 (shown in FIG. 2C). Tubing set 275 could also be made with an IV tubing port. Alternatively, IV tubing 255 may be connected to the heat exchanger 270 through an inlet 252. IV fluids may then pass through and exit the heat exchanger 270 through an outlet 252. The IV tubing 255 connected to the outlet 252 may be placed in fluid connection with extremity 130, such as shown in FIG. 6C. Tubing set 275 may also have a quick connect fitting 276, for connecting the control system 864 (FIG. 8) and the heat exchanger 270. Heat exchanger 270 may also have a fitting for connecting the heat exchanger 270 to the manifold 114. In one embodiment, the heat exchanger 270 is permanently attached to the manifold 114 and/or other portions of the device 200.

Heat exchanger 270 may be configured in a variety of different ways. FIG. 6E illustrates one configuration in which an IV tube 255 is surrounded by an inlet flow path 272 containing a heat exchange fluid and an outlet flow path 271 containing the heat exchange fluid. Multiple such pathways may be provided. Heat exchanger 270 may also be constructed in a shell and tube arrangement, or other similar heat exchanging embodiments. Electrical resistance heating could also be provided. One or more thermocouples could also be provided for monitoring the temperature of IV fluids. In any of the configurations discussed herein, the IV fluid may be adjusted to a desired temperature, such as between about 35° C. and about 40° C., by adjusting the temperature and/or the flow rate of the heat exchanging fluid flowing through the heat exchanger 270 and/or device 200. In one example, the temperature of IV fluid may be regulated to normal human body temperature, such as about 37° C.

In additional embodiments, IV fluid may exchange heat with the heat exchanging fluid, or other heat transfer device, contained in the device 200 and then be delivered to other parts of the patient's body that are not enclosed within the device 200. For example, the IV fluid may be warmed by a device that is used to heat a foot or a leg (e.g., device 600 in FIG. 4), and then the IV fluid may be inserted into an arm. Alternatively, device 200 may be used to regulate both the temperature of a hand and the temperature of IV fluid, however, the IV tubing and IV fluid are connected or inserted into the patient's other arm. Moreover, device 200 may be constructed as a sleeve to regulate temperature of a portion of an appendage, such as a portion of an arm or leg, without also covering the hand or foot, respectively.

Figure 6F:
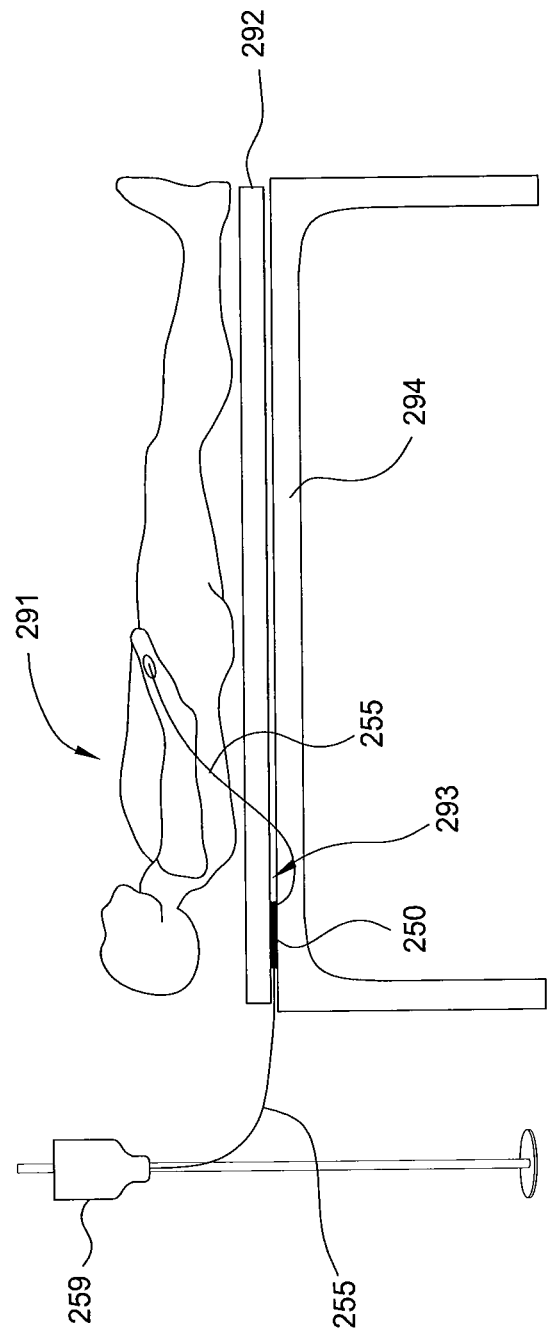
FIG. 6F is a side view of an embodiment of the invention used with a patient.

FIG. 6F illustrates a side view of another embodiment of an IV warming device that is also used to regulate the body temperature of a patient 291. Patient 291 may be placed in proximity to a temperature regulating device 292, such as a heating or cooling pad or blanket. The temperature regulating device 292 may be placed on an operating or examining table 294 on which the patient is positioned. In one embodiment, an IV tubing set 250, which is disposed in an IV regulating device 293, is placed in proximity to or coupled to a portion of the temperature regulating device 292 to warm the IV fluid delivered to the patient 291. In this configuration, the portion of the patient 291 in which the warmed IV fluid is to be inserted need not be in direct contact with the temperature regulating device 292. In one embodiment, the IV regulating device 293 may comprise an IV tubing set 250 that is positioned to exchange heat with the temperature regulating device 292, such as by direct insertion or an attachment to the device, or by being placed in thermal contact with the temperature regulating device 292 by being placed above, below or adjacent to some temperature regulated portion of the temperature regulating device 292.

Control System and Supporting Components

FIG. 7 illustrates an example of a manifold 714 having one or more fittings that are used to connect the various gas, vacuum or fluid lines to various components internal and external to the device 700 according to one or more embodiments of the invention. The manifold 714 can be attached to the one or more body elements and thermal exchange units of the device through one or more apertures on the body elements and the thermal exchange units. FIG. 7 is a partial cut-away view that schematically illustrates a device 700 that contains the various components discussed above in conjunction with the devices illustrated in FIGS. 1-4, and the manifold 714 is useful in any of the configurations discussed herein in. In one aspect, the manifold 714 is used in place of the manifolds 114 and 625 discussed above.

The manifold 714 generally contains one or more fluid ports or pressure ports, such as a pressure port 716, a pressure sensing line 718, a fluid supply line 724, and a fluid return line 722, which can be connected to the manifold body 715 or integrally formed using injection molding, heat stacking, adhesives or other manufacturing methods. Accordingly, quick connect fittings or connectors can be incorporated to provide a connection point to interface the thermal exchange units, fluid pads, other heating components, electric pads, vacuum lines, pressure sensing lines, etc. For example, the manifold 714 may include connectors 730, 732, 734, 736, such as a quick connect type connector similar to CPC Colder Products Company in St, Paul, Minn. In operation, the vacuum space formed in the device 700 requires an robust and airtight seal so that the thermal heat transfer fluids and/or air external to the device doesn't affect the operation of the process. The manifold 714 can be made out of injection molded plastic materials for its low cost, or any other suitable materials. A seal is generally formed between the manifold 714, the various one or more fluid ports or pressure ports (e.g., reference numerals 716, 718), and the body element 710 (e.g., similar to body elements 110, 220) to allow a desired pressure to be reached in the internal region 713 of the device 700 by use of the pump 163. The seal formed between the body element 710 and the various components of the manifold 714 can be created using conventional adhesives, mechanical force, or O-rings to name just a few.

As shown in FIG. 7, the manifold 714 may be connected to the inlet of the thermal exchange units 720A and 720B, which is similar to the devices discussed in conjunction with FIG. 5, using the fluid supply line 724 through one or more fluid supply fittings 754 and conventional tubing 753 that is in fluid communication with the connector 732 and the fluid supply line 161A of the fluid source 161. The outlet of the thermal exchange units 720A and 720B is connected to the fluid return line 722 through one or more fluid supply fittings 752 and conventional tubing 755 that is in fluid communication with the connector 730 and the return fluid line 161B of the fluid source 161.

In one embodiment, the internal region 713 of the device 700 is connected to the pump 163 which is connected to the pressure port 716 that contains a connector 736 contained in the manifold 714, and a fitting 756 that is disposed within the internal region 713 of the device 700. In one aspect, the internal region 713 of the device 700 may also be connected to the vacuum sensor 162 which is connected to the pressure sensing line 718 that contains a connector 734 that is connected to the manifold 714, and a fitting 758 that is disposed within the internal region 713 of the device 700.

In operation, a hand, a forearm, a foot, a leg, an upper extremity, or a lower extremity (not shown) is disposed within the opening 712 of the device 700 and enclosed within the one or more body elements 710 with one or more thermal exchange units 720A, 720B attached thereon and the manifold 714 attached thereto. Alternatively, the device may need to be assembled by folding, rolling one or more body elements and enclosed with one or more enclosing clips. In addition, one or more detachable thermal exchange units may be pre-assembled inside the device or may be assembled upon disposing an extremity into the device. Then, a vacuum sealing portion 741 of the seal element 740 is wrapped around the opening of the device to form a tight seal and prevent air from entering the space between the extremity and the device.

In one embodiment, a fluid sensing assembly 760 is disposed within the fluid supply line 161A to sense the temperature of the fluid entering the one or more thermal exchange units 720A, 720B so that heating or cooling elements contained within fluid source 161 can be controlled by the controller 160. The fluid sensing assembly 760 generally contains a body 762 and one or more sensors 761 (e.g., thermistor, RTD, thermocouple) that are in thermal communication with the fluid being delivered to the one or more thermal exchange units 720A, 720B.

To control the various aspects of the process of increasing the blood flow and temperature control of a mammal, the controller 160 is adapted to control all aspects of the processing sequence. In one embodiment, the controller 160 is adapted to control the fluid source 161, the pump 163, and all other required elements of the device 700. The controller 160 is generally configured to receive inputs from a user and/or various sensors (e.g., vacuum sensor 162, fluid sensing assembly 760) in the device and appropriately control the components in accordance with the various inputs and software instructions retained in the controller's memory. The controller 160 generally contains memory and a CPU which are utilized by the controller to retain various programs, process the programs, and execute the programs when necessary. The memory is connected to the CPU, and may be one or more of a readily available memory, such as random access memory (RAM), read only memory (ROM), floppy disk, hard disk, or any other form of digital storage, local or remote. Software instructions and data can be coded and stored within the memory for instructing the CPU. The support circuits are also connected to the CPU for supporting the processor in a conventional manner. The support circuits may include cache, power supplies, clock circuits, input/output circuitry, subsystems, and the like all well known in the art. A program (or computer instructions) readable by the controller 160 determines which tasks are performable in the device. Preferably, the program is software readable by the controller 160 and includes instructions to monitor and control the process based on defined rules and input data.

Figure 8:
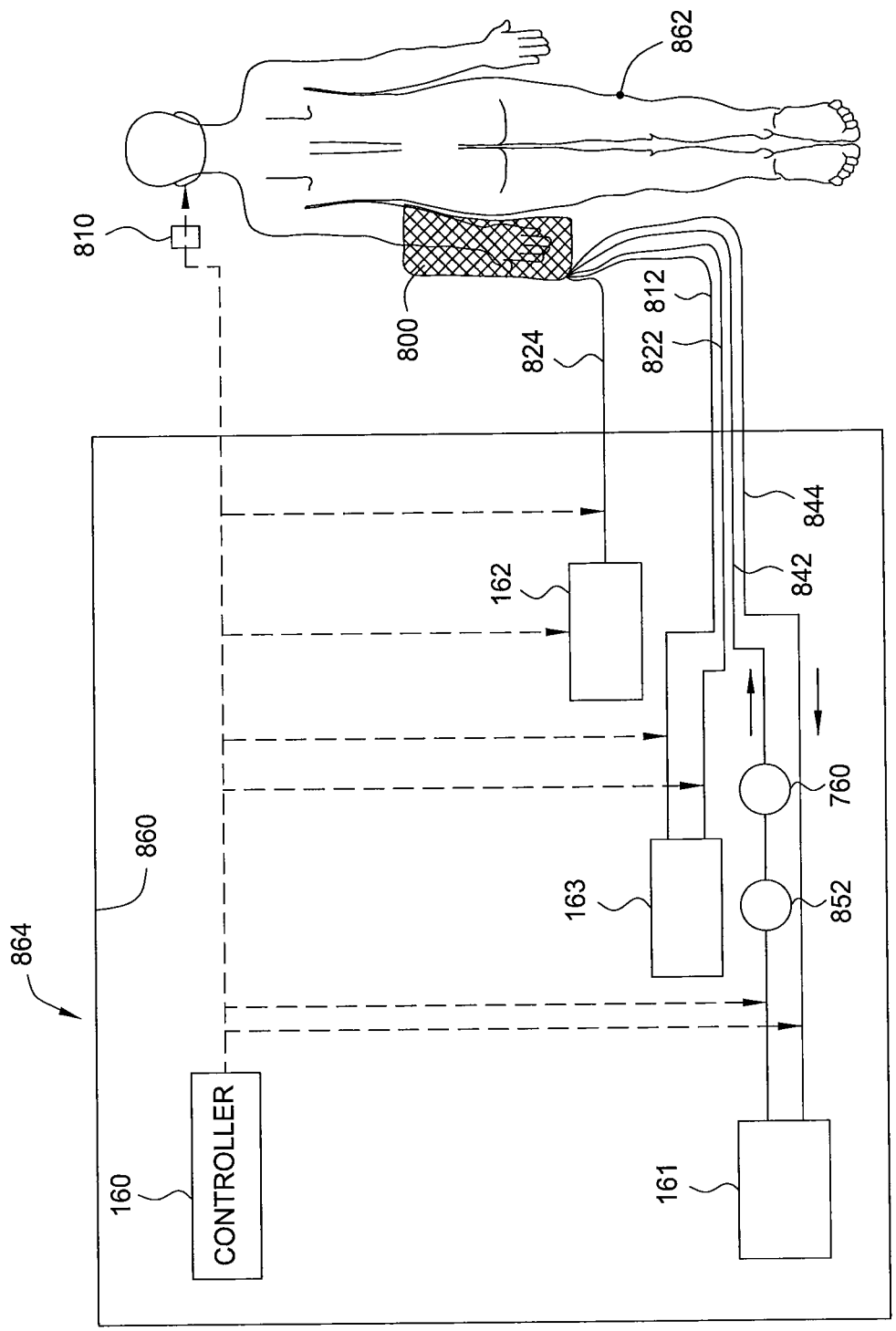
FIG. 8 illustrates one embodiment of a control unit connected to a device according to an embodiment of the invention.

FIG. 8 illustrates one embodiment of the control system 864 that is connected to various parts of a device 800 according to an embodiment of the invention. The device 800 and control system 864 is similar to the devices discussed above and control system 164 discussed above in conjunction with FIGS. 1-7. The control system 864 generally contains a controller module 860 having the controller 160 therein that houses all the electronics and mechanical parts which are required to regulate the temperature, vacuum pressure level, and compression pressurized force provided to the pressurized volume of the device. In this configuration, the control system 864 typically includes, for example, a pump 163, a vacuum sensor 162, conventional tubing 824, a fluid source 161, a fluid flow sensor 852, a fluid sensing assembly 760, and a temperature sensor 810. The temperature sensor 810 is generally a device that is used to measure the temperature of the patient while the process of increasing the blood flow and controlling the temperature of the patient is being performed. Temperature of the patient can be measured in the ear, mouth, on the skin, or rectally using an appropriate conventional temperature sensing device. The control system 864 may also contain a thermal exchange medium pump, a heater, a cooler, thermocouples, a heating medium pump, a proportional-integral-derivative (PID) controller for process control of the vacuum and the temperature, one or more power supplies, display panels, actuators, connectors, among others, that are controlled by the controller 160. The settings and current readings of the various elements in the of the control system 864 may be conveniently positioned onto a display panel (e.g., lighted display, CRT) which provides an operator interface. The controller 160 may contain additional electronics for optimal operation of the device 800 of the invention. In alternative embodiments, the vacuum control and temperature control may be controlled by two different controllers.

The control system 864 may provide safety features including a device shutdown feature that is activated if the device sensors, such as the temperature and pressure sensors, fail or become disconnected. The control system 864 may also include an alarm circuit or an alert signal if the temperature of the apparatus is not regulated correctly. A relief valve may be provided within the vacuum loop of the device such that the chamber may be vented if the vacuum within the chamber exceeds a certain level.

In one embodiment, a temperature probe 862 can be provided to measure the temperature of a portion of a mammal other than a foot, leg, or other extremity where the device is attached to. In another embodiment, a tympanic membrane can be attached to the ear canal as a temperature sensor 810 to provide core temperature reading. As such, a reference temperature for the human, such as a patient, can be obtained. Other sensors may include patient's blood flow and blood pressure and heart rate. These data are important to proper patient health care keeping the patient at normal temperature range and from various thermal maladies. The temperature of the skin in the device could be measured to indicate if the body portion is in a state of vasoconstriction or vasodilatation or what temperature the skin is compared two device fluid temperatures. Temperature of the skin can be measured by different means and different devices like Thermocouples, Thermistor, Heat flux and other measuring devices. Blood flow rate could also be measured and data sent to the controller 160.

As shown in FIG. 8, the device 800 can be connected to the pump 163 (e.g., mechanical vacuum pump, pump and vacuum ejector) via a vacuum port 812 and a vacuum sensor return line 822 to provide a vacuum pressure or a negative pressure inside the device 800. It is important to maintain the vacuum and/or negative pressure levels and correctly sense and read out the vacuum/pressure levels inside the device where the extremity is exposed to and send the data to a vacuum transducer mounted in the controller 160. The vacuum transducer could also be located in the manifold 714 (FIG. 7) allowing for a better response and more accurate control of the vacuum levels. The signal controlling the vacuum pump would come through wires from the vacuum transducer to control circuits in the controller 160. Additional set of data, such as pressure data applied to the extremity by the vacuum, could be measured through a series of pressure sensors placed through the device to record pressure levels and send data to the controller 160 for evaluation. The controller 160 can then adjust the levels of vacuum and the temperature within the device to produce the highest level of blood flow and to increase the body's core temperature as needed.

In addition, the device 800 with one or more thermal exchange units therein may be connected to the fluid source 161 via a thermal exchange medium supply line 842 and a thermal exchange medium return line 844. Further, the flow of a thermal exchange medium flown inside the thermal exchange medium supply line 842 can be monitored and regulated by the fluid flow sensor 852 and/or fluid sensing assembly 760. In addition, a low fluid led may be used and displayed on the front panel of the controller 160 to warn an operator of fluid level in the reservoir of a fluid source. Additional sensor will be added to the fluid reservoir to send a signal when the fluid level is low and more fluid is needed. Further, there may be controlling signal that allow a conventional fluid pump to operate in a mode of returning fluid back from the fluid pads when the procedure or a single operation of the device is complete. Additionally, the device may include a temperature sensor for the heated or cooled fluid circulating through various tubing's and fluid lines. In addition, the thermal exchange units of the invention may include one or more temperature sensors and thermocouples to monitor the temperature of a mammal's extremity and provide temperature control feedback.

In one embodiment, the thermal exchange units are coupled in a closed loop configuration with the fluid source 161 which provides a thermal exchange medium. For example, the thermal exchange unit may be coupled in a closed liquid loop configuration with a liquid tank housed within the controller module 860. In one embodiment, one or more resistive heating elements and/or thermoelectric devices are used to heat or cool the thermal exchange medium contained in the liquid tank. The closed loop configuration reduces the maintenance requirements for the operator because it minimizes the loss of thermal exchange medium that typically occurs if the thermal exchange unit is detached from the thermal exchange medium source.

The embodiments of the apparatus described above provide a method of increasing blood flow in one or more extremities of a mammal and decreasing clots within the veins in order to regulate thermal maladies and/or prevent deep vein thrombosis (DVT). The method includes providing one or more devices of the invention to the mammal and regulating the temperature of the one or more extremities of the mammal using the devices. As a result, one or more Arteriovenous Anastomoses (AVAs) blood vessels inside an extremity of a mammal are vasodilator, and constriction of the AVA blood vessels is reduced, thereby increasing blood flow and blood volume in the one or more extremities, decreasing the vessel wall contact time of the blood flow, and decreasing clots in the veins due to pooling. Any suitable portions of an extremity, preferably an extremity with vasculature that can be vasodilator by the device, may be placed into a device and sealed therein.

Referring to FIGS. 1-2D, the process of using the device 200 discussed above generally starts by positioning an extremity 130 in the internal region 213 of the device 200. While the process of increasing blood flow and the temperature of a mammal is discussed in conjunction with the device 200, this configuration is not intended to be limiting to the scope of the invention since any of the devices discussed herein could be used to perform this process. Once the extremity 130 is enclosed in the device 200, negative pressure is applied to a pressure port 116 thereby lowering the pressure within the internal region 213 and exposing the extremity 130 to decreased pressure in the range, for example, of about 0 to about −20 mmHg, such as from about −10 mmHg to about −14 mmHg. Simultaneously or sequentially, a thermal exchange medium is introduced into one or more thermal exchange units 220 positioned inside the internal region 213 of device 200. The flow rate of the pump 163 may be constant and the flow rate need only be to maintain so that a constant pressure can be achieved in the internal region 213. If there is a slight leak in the system the required flow rate may be greater than about 6 liters per minute, and is preferably about 4 liters per minute or lower. In one aspect, the flow rate of the vacuum pump may be between about 4 liters and about 10 liters per minute, but is preferably less than about 6 liters per minute.

In one embodiment, the controller 160 manages the thermal exchange medium and negative pressure for the duration of the treatment, which may be about 30 minutes, for example. The duration may be longer or shorter depending on the size of the extremity treated and the temperature of the extremity. The process may be repeated one or more times as needed. In some cases, the duration of the treatment may be cycled "on" for a period of time and then "off" for a time period. In one example, the duration of the treatment is about 1 minute or longer and then off for a period of about 1 minute or longer, which is repeated for 5 cycles or more.

Embodiments of the invention may be used to increase blood flow and regulate the temperature of a mammal by increasing the temperature of the thermal exchange medium delivered to the thermal exchange devices to a temperature as high as possible without burning the mammal. In a healthy patient, burning of the cells on the appendage can occur if the cell temperature exceeds about 43 degrees Celsius (° C.), but this may vary with exposure time and rate of thermal transfer. Therefore, the temperature of the thermal exchange medium is preferably calibrated such that skin temperature is maintained at less than 43 degrees Celsius. For example, different people have different tolerance levels for different temperature ranges, according to their ages, health conditions, etc. In general, to heat the extremity it is desirable to control the temperature of the thermal exchange medium and thus the surface of the thermal exchange units to a temperature is between about 30° C. to about 43° C. In one embodiment, the temperature of the thermal exchange medium and thus the surface of the thermal exchange units is between about 37° C. to about 40° C.

In addition, the device can be used to cool the temperature of a patient. In general, a patient's temperature can be maintained, or, if it is required by the procedure, the patient's core temperature can be lowered by active cooling to about 33° C. In general, to cool the extremity it is desirable to control the temperature of the thermal exchange medium and thus the surface of the thermal exchange units to a temperature is between about 0° C. to about 30° C. In one embodiment, the temperature of the thermal exchange medium and thus the surface of the thermal exchange units is between about 0° C. to about 10° C.

Other examples of devices that may be adapted for use with one or more of the embodiments described above is further described in the commonly assigned U.S. patent application Ser. No. 11/870,780, filed Oct. 11, 2007, which is herein incorporated by reference in its entirety.

While the foregoing is directed to embodiments of the present invention, other and further embodiments of the invention may be devised without departing from the basic scope thereof, and the scope thereof is determined by the claims that follow.

What is claimed is:

1. An apparatus for exchanging heat with an extremity of a mammal, comprising:
 a body element having one or more walls that enclose an internal region;
 an opening formed in the body element that is adapted to receive an extremity of a mammal and allow a portion of the extremity to be positioned within the internal region;
 one or more thermal exchanging units that are in thermal contact with the internal region;
 an aperture formed in the body element, wherein the aperture provides access to the portion of the extremity positioned within the internal region; and
 IV tubing disposed in proximity to at least one of the one or more thermal exchanging units, such that the IV tubing is in thermal contact with the one or more thermal exchanging units.

2. The apparatus of claim 1, further comprising a bonding material disposed around the aperture.

3. The apparatus of claim 1, further comprising:
 a bonding material disposed in the internal region and around the aperture formed in the body element; and
 a release liner disposed over a portion of the bonding material.

4. The apparatus of claim 1, wherein the aperture is adapted to receive an IV tube, catheter or sensor cable.

5. The apparatus of claim 1, wherein the aperture is adapted to receive an IV tube, catheter or sensor cable, and further comprises:
 an extremity sealing member that is adapted to form a seal between the body element and a portion of the extremity; and
 a sealing member that is adapted to form a seal over the aperture.

6. The apparatus of claim 1, further comprising a pump that is adapted to control the pressure within the internal region.

7. The apparatus of claim 1, wherein the one or more thermal exchanging units and the body element are both formed from a flexible and compliant material.

8. The apparatus of claim 1, wherein the one or more thermal exchanging units and the body element are an integral element that comprises:
 a first sheet of compliant material; and
 a second sheet of compliant material, wherein the first sheet of compliant material and the second sheet of compliant material are bonded together to enclose at least a portion of the internal region, and form a fluid plenum that is isolated from the internal region.

9. The apparatus of claim 1, further comprising a fluid source that is in fluid communication with a heat exchanging plenum in the one of the one or more thermal exchanging units.

10. The apparatus of claim 1, further comprising:
 a manifold having a first fitting that is in fluid communication with the internal region and a second fitting that is in fluid communication with a fluid plenum formed in one of the one or more thermal exchanging units; and
 a system controller comprising:
  a first pump that is adapted to control the pressure within the internal region when it is in fluid communication with the first fitting;
  a fluid heat exchanger having a thermal exchanging fluid that is adapted to control the temperature of the one or more thermal exchanging units when it is in fluid communication with the one or more thermal exchanging units;
  a pressure sensor that is in fluid communication with the internal region;
  a temperature sensor that is adapted to measure a temperature of the mammal; and
  a controller that is adapted to control the temperature of the fluid heat exchanging fluid and the pressure of the internal region using inputs received from the temperature sensor and the pressure sensor, and control the first pump.

11. The method of claim 1, wherein the body element is formed from a flexible material, and wherein at least a portion of the body element defines an outermost surface of a portion of the apparatus that is disposed over the portion of the extremity.

12. An apparatus for exchanging heat with an extremity of a mammal, comprising:
- a first sheet of compliant material; and
- a second sheet of compliant material, wherein the first sheet of compliant material and the second sheet of compliant material are coupled together to form:
  - at least a portion of an internal region;
  - an opening that is adapted to receive an extremity of a mammal and allow a portion of the extremity to be positioned within the internal region; and
  - a fluid plenum that is isolated from the internal region;
- an aperture in the first sheet of compliant material, wherein the aperture provides access to the portion of the extremity positioned within the internal region;
- a bonding material disposed on a surface of the first sheet of compliant material and around the aperture, wherein the surface defines at least a portion of the internal region; and
- IV tubing disposed in proximity to at least one of the one or more thermal exchanging units, such that the IV tubing is in thermal contact with the one or more thermal exchanging units.

13. The apparatus of claim 12, further comprising a release liner disposed over a portion of the bonding material.

14. The apparatus of claim 13, wherein the bonding material comprises hydrogel.

15. The apparatus of claim 12, wherein the first sheet of compliant material and the second sheet of compliant material each comprise a material selected from a group consisting of urethane, polyurethane, polypropylenes, polystyrenes, high density polyethylene's (HDPE), low density polyethylene's (LDPE), and poly(vinyl chloride).

16. The apparatus of claim 12, further comprising a pump that is adapted to control the pressure within the internal region.

17. A method of exchanging heat with an extremity of a mammal to aid in the placement or advancement of a device into a vascular structure of the mammal, comprising:
- positioning a portion of an extremity of a mammal in an internal region of a body element, wherein the extremity is disposed in the internal region through an opening in the body element;
- transferring heat between the portion of the extremity disposed in the body element and a thermal exchange unit;
- bonding a first portion of the body element to a contact region which surrounds a first region of the surface of the extremity, wherein the first portion of the body element comprises an aperture that exposes the first region of the surface; and
- inserting a catheter into the first region through the aperture and into an artery or a vein found in the extremity.

18. The method of claim 17, wherein the artery is the radial artery or the ulnar artery.

19. The method of claim 17, wherein transferring heat between the portion of the extremity and the thermal exchange unit further comprises controlling the temperature of the portion of the extremity before inserting the catheter through the aperture of the body element.

20. The method of claim 19, further comprising:
- lowering the pressure in the internal region after bonding the portion of the body element to a surface of the extremity.

* * * * *